(12) United States Patent
Carpino et al.

(10) Patent No.: US 6,825,347 B2
(45) Date of Patent: Nov. 30, 2004

(54) URONIUM AND IMMONIUM SALTS FOR PEPTIDE COUPLING

(75) Inventors: Louis A. Carpino, Amherst, MA (US); Hideko Imazumi, Hachinohe Aomori (JP); Ayman El-Faham, El-Gomrolr Alexandira (EG)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 10/152,299

(22) Filed: May 21, 2002

(65) Prior Publication Data
US 2003/0125561 A1 Jul. 3, 2003

Related U.S. Application Data

(60) Provisional application No. 60/292,375, filed on May 21, 2001.

(51) Int. Cl.[7] .................. C07D 237/26; C07D 239/70; C07D 279/18
(52) U.S. Cl. ...................... 544/235; 544/253; 544/262; 544/35
(58) Field of Search ............... 544/235, 253, 544/262, 35

(56) References Cited

U.S. PATENT DOCUMENTS 5,644,029 A * 7/1997 Carpino ............ 530/333
6,046,136 A    4/2000 James et al.
6,075,016 A    6/2000 Chasin et al.
RE37,686 E    4/2002 Carpino

OTHER PUBLICATIONS

El–Faham, CA 125:11428, abstract of Bull of Faculty of Science, Alexandira University, 1996, vol 36(1), pp 73–80.*

Descristoforo, CA 133:331508, J of Nuclear Medicine, 2000, vol 41(6), pp 1114–1119.*

Carpino, Organic Letters, vol 3(18), pp 2793–2795, 2001.*

* cited by examiner

*Primary Examiner*—D. Margaret Seaman
(74) *Attorney, Agent, or Firm*—Scully, Scott, Murphy & Presser

(57) ABSTRACT

The present invention is directed to salts of the formula:

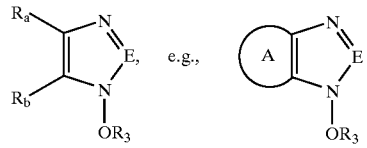

or N-oxides thereof, and their use in preparing an amide.

59 Claims, No Drawings

URONIUM AND IMMONIUM SALTS FOR PEPTIDE COUPLING

CROSS REFERENCE TO RELATED APPLICATION

This application claims priority of U.S. Provisional Application Ser. No. 60/292,375 filed on May 21, 2001.

GOVERNMENT SUPPORT

This work has been supported by a grant from the National Institutes of Health GM-09706 and the National Science Foundation (CHE-9707651). The Government has certain rights in the invention.

BACKGROUND OF THE INVENTION

1. Field of the Invention

The present invention relates to uronium and immonium salts and their use in effecting the acylation step in amide formation, especially during peptide synthesis.

2. Description of the Prior Art

Polypeptides are useful as medicaments. In recent years, peptides have been found to be useful in combating various diseases, such as cancer, diabetes, plant toxins and the like. Additionally, peptides have shown specific activity as growth promoters, suppressants, antibodies, insecticides, contraceptives, anti-hypertensives, sleep-inducers, antidepressants, analgesics, etc. The list is long and varied.

As more and more polypeptides become of medicinal importance, there is an increasing incentive to improve the methods by which they may be synthesized. Currently, syntheses of peptides are in solution by classical or various repetitive methods. Alternatively, peptides may be prepared on a solid support (Merrifield method). These are all popular techniques in synthesizing peptides from the coupling of two or more amino acids, in synthesizing larger peptides from the coupling of amino acids with smaller peptides or in the coupling of smaller peptides. Solution methods have the advantage of being easily monitored, allowing purification of intermediates, if necessary, at any stage. A major drawback, however, is the relative slow pace of synthesis, with each step being carried out manually.

The major advantage of the Merrifield method is its easy automation so that unattended, computer-controlled machine synthesis is possible. Unfortunately, the method suffers from an inherent deficiency due to the insoluble nature of the support on which the synthesis proceeds. Unless each acylation step occurs with approximately 100% efficiency, mixtures will inevitably be built up on the polymer. The longer the chain, the greater will be the contamination by undesired side reactions. Side products produced in such reactions remain to contaminate the desired product when it is removed from the polymeric matrix at the end of the cycle. These current techniques are not useful in preparing peptides of greater than 30–40 residues; separation of side products from the desired product becomes increasingly difficult when larger peptides are synthesized.

For very long segments (60 or more amino acids), therefore current methods are not satisfactory. Often, mixtures are obtained of such forbidding complexity that it may be difficult or impossible to isolate the desired peptide.

The problems enumerated hereinabove may be eliminated if the proper derivatives of the underlying amino acids and/or the proper conditions for the coupling reaction could be found. Protecting groups, such as t-butyloxycarbonyl (t-Boc) or N-α-(9-fluorenylmethyl)oxycarbonyl (Fmoc), have been used to minimize side reactions. But, additionally, other aspects of the coupling reaction must also be taken into consideration, such as the peptide coupling additive to be used in the coupling reaction.

Additives generally inhibit side reactions and reduce racemization. Heretofore, the most common peptide coupling additive used during peptide coupling for both solutions and solid phase synthesis is 1-hydroxybenzotriazole (HOBt). This reagent has been used either in combination with a carbodimide or other coupling agent or built into a stand-alone reagent, such as 1-benzotriazolyoxytris(dimethylamino)phosphonium hexafluorophosphate (BOP) or an analogous uronium salt. HOBt is applicable to both stepwise and segment condensations. However, many cases have been encountered in which HOBt is ineffective, possibly because of stearic effects, or low basicity of the amino component. Especially problematic are segment coupling at amino acid units other than glycine or proline, since the problem of racemization may be severe. The related N-hydroxybenzotriazinone (HOOBt) may provide better protection against racemization, but it is rarely used due to competing side reactions involving ring openings.

Other reagents for facilitating peptide coupling have also been described. For example, in *Tetrahedron Letters*, 1994, 35, 2279–2282, Carpino, et al. disclose that 1-hydroxy-7-azabenzotriazole and its corresponding uronium salts, designated HAPyU and AOP were effective in promoting peptide coupling and avoiding racemization in a model solid-phase peptide segment coupling process. In addition, Carpino, et al. disclose in *J. Org. Chem.*, 1994, 59, 695–698 that azabenzotriazolyluronium salts, e.g., designated as HBTU, HATU, HBPyU, HAPyU, HBMDU and HAMDU, are useful in peptide synthesis. Other publications such as Ehrlich, et al., disclose that the uronium salts, designated as HAPyU and TAPipU were useful for promoting peptide cyclization with a minimum of racemization.

U.S. Pat. No. 5,644,029 to Carpino discloses among other things, the use of compounds of the following formula in promoting peptide coupling:

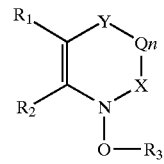

and N-oxides thereof and salts thereof wherein
  $R_1$ and $R_2$ taken together with the carbon atoms to which they are attached form a heteroaryl ring wherein said heteroaryl ring is an oxygen, sulfur or nitrogen containing heteroaromatic containing from 3 and up to a total of 13 ring carbon atoms, said heteroaryl may be unsubstituted or substituted with lower alkyl or an electron-donating group;
  Y is O, $NR_4$, $CR_4R_5$;
  $R_5$ is independently hydrogen or lower alkyl;
  X is $CR_6R_7$ or $NR_6$;
  $R_6$ and $R_7$ are independently hydrogen or lower alkyl; or $R_6$ and $R_7$ taken together form an oxo group or when n=0, $R_4$ and $R_6$ taken together may form a bond between the nitrogen or carbon atom of Y and the nitrogen or carbon atom of X;
  Q is $(CR_8R_9)$ or $(NR_8)$;

when n is 1, $R_4$ and $R_8$ taken together may form a bond between the ring carbon or nitrogen atom of Q and the ring carbon or nitrogen atom of $R_8$;

n is 0, 1 or 2;

$R_3$ is hydrogen, lower alkyl carbonyl, aryl carbonyl, lower aryl alkyl carbonyl,

—C(=O)—AA₁—BLK₁, a positively charged electron withdrawing group, $SO_2R_{14}$, or

[structure with $R_1$, $R_2$, Y, X, $(CH_2)_n$, $(CH_2)_q$]

$R_{14}$ is lower alkyl, aryl or lower arylalkyl; q is 0–3;

$R_8$ and $R_9$ are independently hydrogen or lower alkyl or $R_7$ and $R_8$ taken together with the carbon to which they are attached form an aryl ring, $AA_1$ is an amino acid and BLK is an amino protecting group, and m is 0 or 1.

It teaches that the compounds are prepared by reacting compounds of the formula:

[structure with $R_1$, $R_2$, Y, Q_n, X, N, OH]

with $R_3L$ in the presence of a base under substitution reaction conditions, in which $R_1$, $R_2$, Y, Q, n, X, and $R_3$ are as defined hereinabove and L is a leaving group, such as halide.

At the time of the publications of the aforementioned articles as well as of the time of the filing of the aforementioned patent, it was believed that all of the compounds described therein had the formula shown hereinabove wherein the $R_3$ was bonded to the oxygen atom (the O-isomer). This belief was based upon the structure of the corresponding phosphonium derivatives, such as benzotriazol-1-yl-N-oxy-tris(dimethylamino) phosphonium hexafluorophosphite (BOP)

[BOP structure with $PF_6^-$]

and benzotriazol-1-yl-N-oxy-tris-(pyrrolidino)-phosphonium hexafluorophosphate

[structure with $PF_6^-$]

in which the oxygen atom was bonded to the cationic phosphonium group. Based on these structures, when the uronium salt derivatives of hydroxybenzotriazole were first described it was assumed, by the scientific community by analogy, to have the structure hereinbelow:

[structure with $PF_6^-$, O—C(NMe₂)₂]

wherein the positively charged uronium ion was bonded to the oxygen atom.

In addition, when other coupling reagents, such as HATU were described, by analogy to the structures assigned to the hydroxybenzotriazole derivatives, it was also assumed that HATU and its derivatives also had the structure:

[structure with $PF_6^-$, O—C(NMe₂)₂]

In fact, based on the same assumptions, it was believed that the uronium salts in general, for example, described hereinabove in the aforementioned publications had similar structures wherein the oxygen atom was bonded to the positively charged cation. Because such structures were believed to be the O-isomers, x-ray crystallography of these new O-isomers was not performed.

However, finally when x-ray crystallography was finally taken of the structures of HBTU and HATU, it was surprisingly learned that the assumption was incorrect with respect to the uronium salt derivatives. More specifically, it was later learned from X-ray crystallographic analysis that the structure assigned to HATU and HBTU were not the structures indicated hereinabove. More specifically, the positively charged moiety is not attached to the oxygen atom, but instead is substituted on the nitrogen atom of the triazole, having the structure shown hereinbelow:

[structure with C(NMe₂)₂, $PF_6^-$]

wherein X=N or CH. In the triazole derivatives depicted hereinabove, this phenomenon wherein the positively charged group was on the nitrogen atom only appeared to occur when $R_3$ in the structure above was an electron withdrawing group which contained a positively charged nitrogen atom.

However, the situation was even more complex. The present inventors noticed that when the 1-hydroxy-4-methyl-7-azabenzotriazole was reacted with 2-chloro-1,1,3,3-bis tetramethylene uronium hexafluorophosphate in the presence of a weak base, an interesting phenomenon occurred. Sometimes, they obtained the product

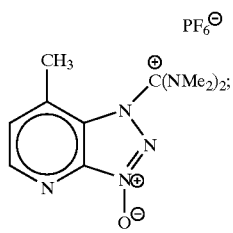

But, other times, they obtained the product,

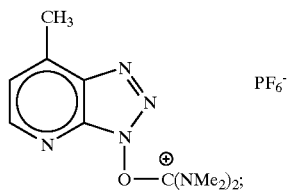

and sometimes they obtained a mixture of the two. Even though the present inventors had conducted the reaction using the same reagents, the products obtained were not always the same. Until recently, the present inventors could not explain these different results with the 4-methyl derivatives, and the inventors did not understand or know how to make the O or the N-isomer of the 4-methyl derivative with any consistency.

Thus, it was concluded that in general, with respect to the triazole derivatives or triazole like derivatives, when $R^3$ is a positively charged electron withdrawing group containing a positively charged nitrogen atom such as an amino cation or an uronium group, the product prepared in accordance with the methodology described hereinabove was not the O-isomer (i.e., the product in which the $R_3$ group is attached to the oxygen atom), but rather the N-isomer (i.e., the product in which the $R_3$ group is attached to the nitrogen atom). Thus, to date, when $R_3$ is an uronium cation or immonium cation, the N-isomer has been prepared, but the corresponding O-isomer has not been prepared.

Based upon this revelation, there were concerted efforts in the scientific community to make the elusive O isomer for HOAT and HOBT immonium and uronium type coupling agents. For instance, Li and Xu alleged that they have found a means of making O isomers of various HOBT and HOAT immonium type coupling reagents, which were prepared in situ and which were useful in peptide coupling. For example, it was alleged but not confirmed by Li and Xu in *Tetrahedron* 56, 4437–4445 (2000) and in *Tetrahedron Letters*, 41, 721–724 (2000), that the reaction of the hydroxy triazole in the presence of $SbCl_6$, would produce the O-isomer of HOBt or HOAT based immonium type reagents, such as those shown hereinbelow:

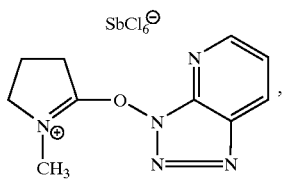
AOMP

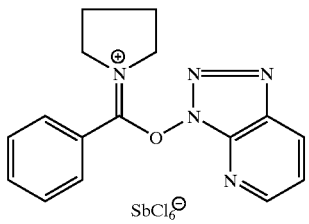
BPMP

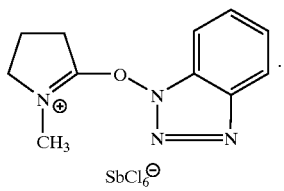
BDMP

However, the x-ray diffraction determined that they did not make the analogous O isomer derivative shown hereinbelow:

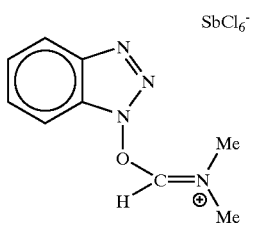

but rather the N-isomer

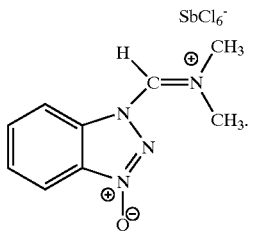

Moreover, when they took the x-ray analysis of another one of the compounds, namely BDMP, which they originally believed was the O-isomer, as drawn hereinabove, they also found that they did not make the O-isomer depicted hereinabove, but rather the corresponding N-isomer. See, Li and Xu, *J. Chem. Soc. Perkin Trans.*, 2, 113–120 (2001). To date, they have not confirmed the structures of the other O-isomer products, which they have proposed.

Thus, to date, no one has actually prepared the O-isomers of the uronium salts and immonium salts of the HOAt or HOBt compounds.

However, the present inventors have found a means of synthesizing the O-isomers and have shown that the O-isomer is also useful for peptide coupling.

SUMMARY OF THE INVENTION

Accordingly, the present invention is directed to a compound of the formula:

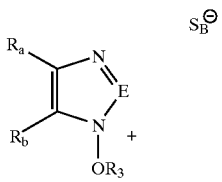

wherein $R_3$ is a positively charged electron withdrawing group having the formula:

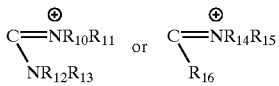

$R_{10}$, $R_{11}$, $R_{12}$, $R_{13}$, $R_{14}$, $R_{15}$, $R_{16}$ are independently hydrogen or lower alkyl which may be unsubstituted or substituted with an electron withdrawing or electron donating group, or $R_{10}$ and $R_{12}$ taken together with the nitrogen atom to which they are attached and the carbon atom attached to the nitrogen atoms form a 5 or 6 membered nitrogen containing heterocyclic containing 3 or 4 ring carbon atoms, respectively or $R_{10}$ and $R_{11}$ taken together with the nitrogen atom to which they are attached or $R_{12}$ and $R_{13}$ taken together with the nitrogen atom to which they are attached form a 5 or 6-membered heterocyclic ring containing up to 5 ring carbon atoms respectively or $R_{14}$ and $R_{15}$ taken together with the nitrogen atom to which they are attached form a 5 or 6-membered heterocyclic ring containing 4 or 5 ring carbon atoms, respectively or $R_{14}$ taken together with the nitrogen to which it is attached and $R_{16}$ taken together with the carbon atoms attached thereto form a 5 or 6 membered nitrogen containing heterocyclic ring, containing 4 or 5 ring carbon atoms, respectively;

E is N or CR;

R is hydrogen or lower alkyl;

$S_B$ is an anion;

$R_a$ and $R_b$ are independently hydrogen, lower alkyl, an electron withdrawing group or electron donating group or $R_a$ and $R_b$ taken together with the carbon atoms to which they are attached form a cycloalkyl group, a heterocyclic group, an aryl group or a heteroaryl group, which cycloalkyl, heterocyclic, aryl and cycloalkyl groups are unsubstituted or substituted by lower alkyl, an electron withdrawing group or an electron donating group.

In a preferred embodiment, the cation portion of the salt of Formula I has the formula:

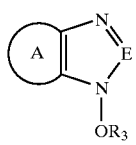

or the N-oxides thereof or the salts thereof wherein

A is an aryl group containing 6–14 ring carbon atoms and up to a total of 20 carbon atoms or a heteroaryl ring, where said heteroaryl ring is an oxygen, sulfur or nitrogen containing heteroaromatic having from 5 and up to a total of 14 ring atoms and from 3 up to a total of 13 ring carbon atoms and up to a total of 20 carbon atoms, said heteroaryl and aryl groups may be unsubsituted or substituted with an electron donating or electron withdrawing groups or lower alkyl;

$R_3$ is a positively charged electron withdrawing group having the formula:

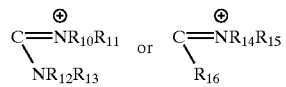

$R_{10}$, $R_{11}$, $R_{12}$, $R_{13}$, $R_{14}$, $R_{15}$, $R_{16}$ are independently hydrogen or lower alkyl which may be unsubstituted or substituted with an electron withdrawing or electron donating group, or $R_{10}$ and $R_{12}$ taken together with the nitrogen atom to which they are attached and the carbon atom attached to the nitrogen atoms form a 5 or 6 membered nitrogen containing heterocyclic containing 3 or 4 ring carbon atoms, respectively or $R_{10}$ and $R_{11}$ taken together with the nitrogen atom to which they are attached or $R_{12}$ and $R_{13}$ taken together with the nitrogen atom to which they are attached form a 5 or 6-membered heterocyclic ring containing up to 5 ring carbon atoms respectively or $R_{14}$ and $R_{15}$ taken together with the nitrogen atom to which they are attached form a 5 or 6-membered heterocyclic ring containing 4 or 5 ring carbon atoms, respectively or $R_{14}$ taken together with the nitrogen to which it is attached and $R_{16}$ taken together with the carbon atom to which it is attached form a 5 or 6 membered nitrogen containing heterocyclic ring, containing 4 or 5 ring carbon atoms, respectively;

E is N or CR; and

R is hydrogen or lower alkyl.

Another embodiment of the present invention is directed to an isolated product of Formula I or II.

In a preferred embodiment the compound of Formula I or II is substantially pure.

The present invention is also directed to a process of preparing an amide, including a peptide, which comprises reacting an amine with a carboxylic acid in the presence of an amide forming effective amount of a compound of Formula I or II, and optionally in the presence of a dehydrating reagent.

DETAILED DESCRIPTION OF THE INVENTION

As described hereinabove, an embodiment of the present invention relates to a compounds of Formula I and II and their use in preparing amides, such as peptides. With respect to the formation of peptides, the compound of Formula I and II can be used in forming peptides wherein a first amino acid or a first peptide, each having a free amino group is coupled with a second amino acid or a second peptide each having a free carboxy group under amide forming conditions to form a peptide. In the case wherein one of the reactants is a peptide, the resulting product is a larger peptide.

As used herein, the term "cycloalkyl" group denotes a cyclic moiety containing 8 to 13 ring carbon atoms and up to a total of 20 carbon atoms. The cycloalkyl group may be completely saturated or may contain carbon-carbon double bonds, more preferably, no more than about 3 carbon-carbon double bonds, and more preferably each contain 0 to 3 carbon-carbon double bonds, and no triple bonds. They may contain 1, 2 or 3 rings. They may be unsubstituted or substituted with 1 or more electron donating or electron withdrawing groups.

As employed herein, the term "aryl" is an aromatic group containing 4n+2 ring carbon atoms, wherein n is preferably 1, 2 or 3. The aryl group may be unsubstituted or substituted, the total number of carbon atoms present is up to 20 carbon atoms, and more preferably up to 15 carbon atoms. The aryl group may be unsubstituted or it may be substituted with electron donating groups, electron withdrawing groups or loweralkyl. Examples of aryl groups include phenyl, 2-naphthyl, βD-naphthyl and the like. The most preferred aryl group is phenyl.

As used herein, the term "arylalkyl" refers to aryl groups attached to the main chain through an alkylene bridge, wherein said alkylene bridge contains 1–6 carbon atoms. Such groups include benzyl, phenethyl and the like. Moreover, arylalkyl may be unsubstituted or substituted with electron donating or electron withdrawing groups, especially on the aryl portion as defined herein.

As employed herein, the term "heterocyclic" refers to a cycloalkyl group, as defined herein wherein at least one ring carbon atoms is replaced by a S, N or O atom. Preferably, the heterocyclic group contains 5 to 14 ring atoms and up to a total of 13 ring carbon atoms and a total of 18 carbon atoms. Preferably, the heterocyclic group is monocyclic, bicyclic or tricyclic. It is preferred that the heterocyclic group contains no more than 4 ring heteroatoms and more preferably no more than two ring heteroatoms and most preferably one ring heteroatom. Examples include piperidine, tetrahydrofuran, morpholine, tetrahydropyrrole and the like.

As employed herein, the term "heteroaryl" is a heteroaromatic containing at least one heteroatom ring atom selected from nitrogen, sulfur and oxygen. The heteroaryl group preferably contains from 5 to 14 ring atoms and up to a total of 13 ring carbon atoms and a total of 18 carbon atoms. Also included within the term heteroaryl are benzoheterocyclic. Preferably, the heteroaryl ring contains 1, 2, 3 or 4 ring heteroatoms. More preferably, the heteroaryl group may be monocyclic, bicyclic or tricyclic. The heteroaryl group preferably contains no more than two ring heteroatoms, and most preferably contains one ring heteroatom. The most preferred ring heteroatoms are oxygen and nitrogen, with nitrogen being the most preferred. Examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, p-teridinyl, carbolinyl, isothiazolyl, benzofaryl, and the like.

If nitrogen is a ring atom, N-oxides, can also be formed. The present invention contemplate the N-oxides of the nitrogen containing heteroaryls.

As used herein, the term "lower alkyl" when used alone or in combination with other groups, refers to an alkyl group containing from one to six carbon atoms. It may be straight chained or branched and includes such groups as methyl, ethyl, propyl, isopropyl, n-butyl, sec-butyl, isobutyl, t-butyl, n-pentyl, amyl, hexyl and the like. The preferred alkyl group contains from 1–3 carbon atoms and is most preferably methyl.

As used herein, an "electron donating group" shall designate a group that will release or donate electrons more than hydrogen would have if it occupied the same position in the molecule. See, J. March, Advanced Organic Chemistry, 3$^{rd}$ Ed., John Wiley & Sons, p. 238 (1985). These types of groups are well known in the art. Examples include loweralkylamino, diloweralkylamino, amino, aryl, lower alkoxy, loweraralkoxy, aryloxy, mercapto, loweralkylthio and the like. The preferred electron donating groups are amino, hydroxy, loweralkoxy, loweralkylamino and diloweralkylamino.

The term "electron withdrawing group", as defined herein, refers to a group that will draw electrons to itself more than a hydrogen atom would if it occupied the same position in the molecule. See, J. March, Advanced Organic Chemistry, 3$^{rd}$ Ed., John Wiley & Sons, p. 17 (1985). They include such groups as nitro, carboxy, lower carboalkoxy, carboxamido, monohaloalkylalkyl, dihaloalkyl, trihaloalkyl (e.g., $CF_3$), halo, formyl, lower alkanoyl, lower alkyl sulfinyl, lower alkylsulfonyl, and the like.

As indicated hereinabove, the present invention is directed to salts of Formula I:

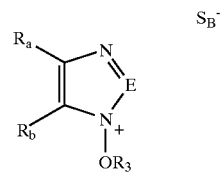

wherein $R_a$, $R_b$, E, $S_B$ and $OR_3$ are as defined hereinabove.

In one embodiment of the present invention $R_a$ and $R_b$ are independently hydrogen or the above-identified substituents on the ring as defined hereinabove.

In another embodiment, $R_a$ and $R_b$ taken together with the carbon atoms to which they are attached form a cycloalkyl group, an aryl group, a heterocyclic group or an heteroaryl group, as these are defined herein. These cyclic groups may be unsubstituted or substituted with one or more electron withdrawing groups or one or more electron donating groups.

The preferred compounds of the present invention are those of Formula II.

As defined herein, A is an aryl or heteroaryl ring. It may be monocyclic, bicyclic or tricyclic. It is fused to the diazole (when E is CR) or triazole (when E is N). It may be unsubstituted or substituted with lower alkyl, or one or more electron donating or electron withdrawing groups, as defined herein. The preferred A groups are phenyl and pyridyl, especially 1- or 4-pyridyl, wherein the nitrogen atom is adjacent to the carbon atom which is shared by both the pyridyl and the diazole or triazole ring.

The preferred values of E are CH and N, with N being most preferred.

$R_3$ is defined herein as a positively charged uronium cation or imino cation. $R_3$ may be acyclic or it may be cyclic. If $R_3$ is acyclic then $R_{10}$, $R_{11}$, $R_{12}$, $R_{13}$, $R_{14}$, $R_{15}$ and $R_{16}$ are independently hydrogen or alkyl. If alkyl, it is preferred that $R_3$ is a straight chain. In addition, it is preferred that if $R_3$ is alkyl, the alkyl contains 1–5 carbon atoms, such as methyl, ethyl, n-propyl, n-butyl or n-pentyl. It is especially more preferred that if $R_3$ is alkyl, the alkyl contains 1–3 carbon atoms. It is also preferred that if the alkyl group in $R_{10}$, $R_{11}$, $R_{12}$, $R_{13}$, $R_{14}$, $R_{15}$ and $R_{16}$ are substituted, it is substituted with an electron donating substituent, especially lower alkoxy. For example, if the alkyl is substituted, a preferred value of $R_{10}$, $R_{11}$, $R_{12}$, $R_{13}$, $R_{14}$, $R_{15}$ and $R_{16}$ is $CH_2CH_2$—O—$CH_2CH_3$. It is more preferred that $R_{10}$, $R_{11}$ and $R_{12}$ and $R_{13}$ are the same and that $R_{14}$, $R_{15}$ and $R_{16}$ are the same.

However, $R_3$ may be a cyclic group. For example, preferred cyclic uronium and imino groups have the formula:

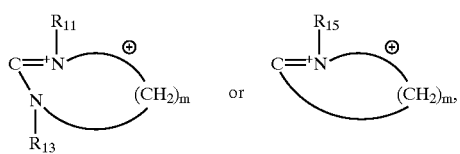

wherein n is 2 or 3 and m is 3 or 4.

Alternatively, with respect to the uronium substituent, $R_{10}$ and $R_{11}$ taken together with the nitrogen atom to which they are attached or $R_{12}$ and $R_{13}$ taken together with the nitrogen atom to which they are attached form a 5 or 6 membered ring. In such a case, they form a ring of the formula:

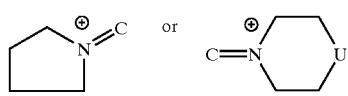

wherein U is $CH_2$, O or N-Alk and Alk is lower alkyl especially methyl.

In such a case $R_3$ becomes:

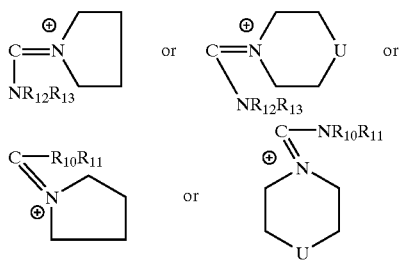

wherein $R_{10}$, $R_{11}$, $R_{12}$ and $R_{13}$ and U are as defined hereinabove.

With respect to the uronium cations, the $R_3$ group may contain two such rings, which may be the same or different, e.g.,

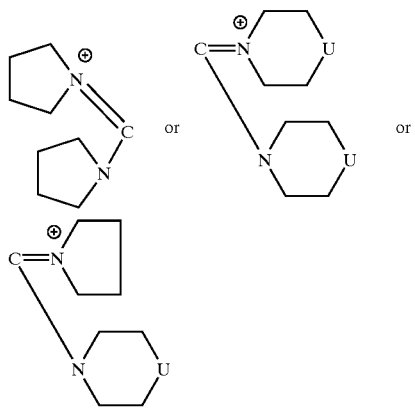

However, if $R_{10}$, $R_{11}$ and the nitrogen atom to which they are attached and $R_{12}$ and $R_{13}$ and the nitrogen atom to which they are attached both form a ring, it is preferred that the rings formed by the two groups are the same.

With respect to the imino cation, the $R_3$ substituent may be substituted as described hereinabove. Alternatively, $R_3$ may be

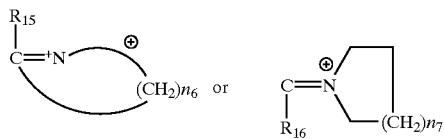

wherein $n_6$ is 2 or 3 and $n_7$ is 1 or 2. For example, $R_{14}$ and $R_{15}$ and the nitrogen atom to which they are attached may form a ring, e.g.,

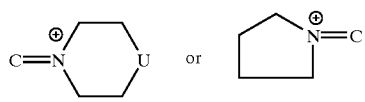

wherein U is as defined hereinabove. Thus, for example, $R_3$ may be

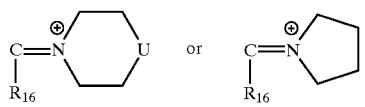

wherein U and $R_{16}$ are as defined hereinabove. Alternatively, $R_{16}$ when combined with the carbon atom and $R_{14}$ combined with the nitrogen atom to which it is attached may form a ring

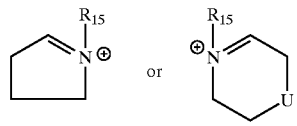

wherein $R_{15}$ and U are as defined hereinabove.

It is preferred that $R_3$ is

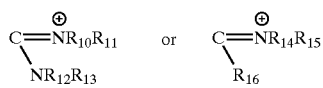

wherein $R_{10}$, $R_{11}$, $R_{12}$ and $R_{13}$ are as defined hereinabove and $R_{14}$, $R_{15}$ and $R_{16}$ are independently hydrogen or lower alkyl which may be unsubstituted or substituted as defined hereinabove. It is even more preferred that $R_3$ is an uronium atom, that is $R_3$ is

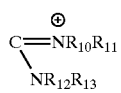

wherein $R_{10}$, $R_{11}$, $R_{12}$ and $R_{13}$ are as defined herein.

The compounds of the present invention preferably have the formula:

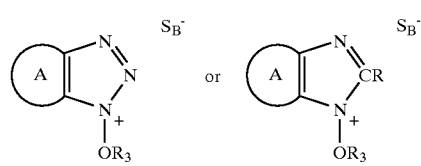

wherein R and $R_3$ are as defined hereinabove.

As defined herein, A is fused to the diazole or triazole ring. A may consist of 1 ring or it may consist of two or more fused rings. It can either be an cycloalkyl, heterocyclic, aryl or heteroaryl ring, which may be unsubstituted or substituted with lower alkyl, an electron donating group or an electron withdrawing group. It is preferred that it is aryl or heteroaryl. If the A ring contains a 6 membered cyclic ring fused to the diazole or triazole, it is preferred that it is not substituted at the 4-position by alkyl or halo. In this case, it is even more preferred that the 4-position is not substituted by any substituent. However, if the A ring contains a 5-membered cyclic ring fused to the diazole or triazole, the 4-position may be unsubstituted or substituted, however, it is preferred that the 4-position is not substituted by alkyl or halo, it is even more preferred that the 4-position is unsubstituted. It is most preferred that the A ring is not substituted. As used herein, the term "substituted at the 4-position" refers to a substituent at the 4-position; however it does not refer to a cyclic group that is part of the A group, having a first cyclic ring fused to the diazole or triazole and a second cyclic ring fused to the first cyclic ring at the 4,5-position thereof.

In a preferred embodiment, the cation portion of the salt of Formula I has the formula:

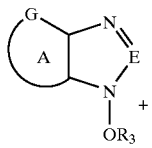

wherein

G is CH or N, and A, E and $R_3$ are as defined hereinabove.

In one embodiment, G is located at position 4 of the ring especially a six-membered ring, and is preferably not substituted.

It is preferred that A is a phenyl ring or a 5 or 6 membered heteroaryl group. If A is a 5 membered heteroaryl, it is preferred that G is CH; if A is a 6 membered heteroaryl, it is preferred that G is N or CH. It is preferred that G is CH. It is preferred that A is phenyl or pyridyl, e.g., 1–2, 3, or 4-pyridyl, i.e.,

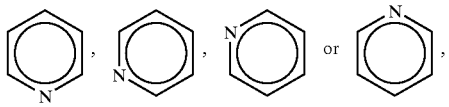

respectively.

The preferred pyridyl is

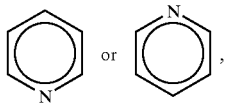

but especially

It is preferred that the pyridyl is not substituted in the 4 position, e.g., it does not have an alkyl or halo substituent thereon. In a more preferred embodiment, it is not substituted by alkyl and in the most preferred embodiment, it is unsubstituted.

Preferred salts of Formula II have the formula:

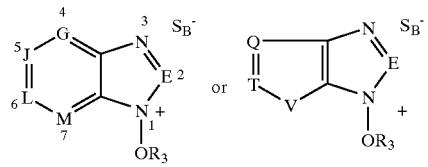

wherein E and $R_3$ are as defined hereinabove

G is N or $CR_1$;

J is N or $CR_2$;

L is N or $CR_8$;

M is N or $CR_5$;

Q is N or $CR_6$;

T is N or $CR_7$;

V is O, S or N;

$R_2$, $R_5$, $R_6$, $R_7$ and $R_8$ are independently hydrogen or lower alkyl or an electron withdrawing group or electron donating group; and $R_1$ is hydrogen.

It is preferred that $R_2$, $R_5$, $R_6$, $R_7$ and $R_8$ are independently hydrogen or lower alkyl. It is even more preferred however that $R_2$, $R_5$, $R_7$, and $R_8$ are as indicated hereinabove and $R_6$ is hydrogen. It is most preferred that $R_2$, $R_3$, $R_5$, $R_6$, $R_7$ and $R_9$ are hydrogen.

Other preferred cation embodiments of the salts of the present invention have the formula:

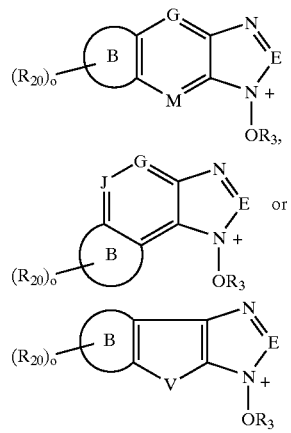

wherein

G, M, J, L, M, E, V, and $R_3$ are as defined hereinabove, $R_{20}$ is hydrogen or lower alkyl which is unsubstituted or substituted with an electron donating group or electron withdrawing group and o is 1, 2, 3 or 4 and B is an aryl, cycloalkyl or heteroaryl ring or heterocyclic ring as defined hereinabove. B may be heterocyclic or heteroaryl, in which 1 or 2 or 3 ring carbon atoms of cycloalkyl or aryl, respectively, may be replaced with a heteroatom selected from the group consisting of N, O or S. It is preferred that B is aryl or heteroaryl.

It is to be noted that when o is 0, then the aryl, heteroaryl heterocyclic or cycloalkyl ring is unsubstituted; and when o is 1, then the ring is monosubstituted; and when o is 2, then the ring is disubstituted and so forth.

Preferred cations include

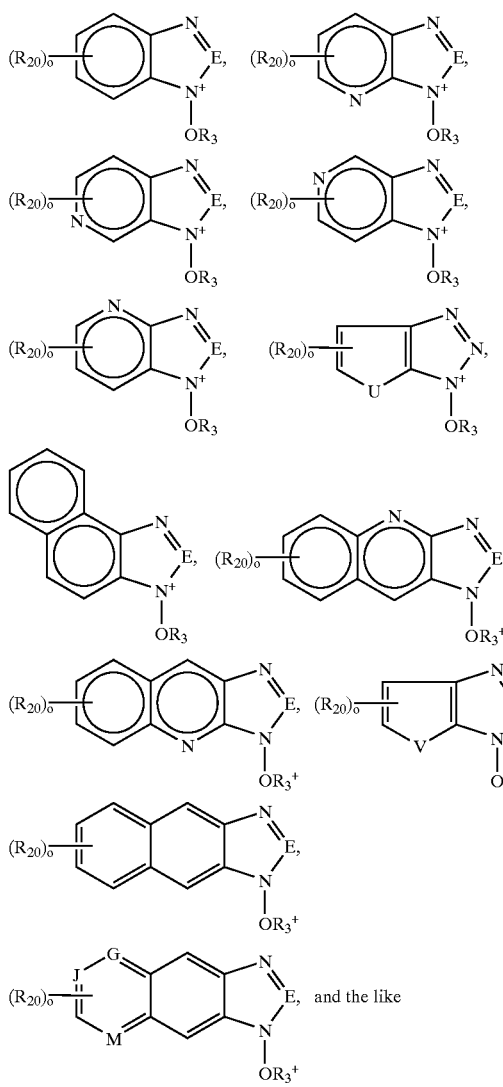

and wherein one of J, G, L, M is N and the remainder is CH, and $R_{20}$, E and o are as defined hereinabove.

Especially preferred embodiments include

HBTU

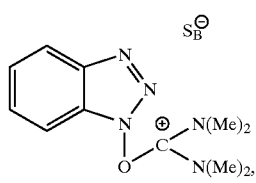

HATU

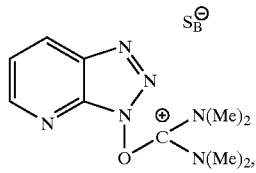

O-HBPyU

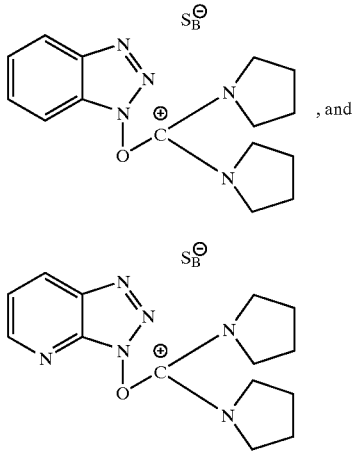
, and

O-HAPyU where $S_B^-$ is an anion (counter anion).

Of course, various combinations and permutations of the formulae described herein are also contemplated by the present invention. In addition, Markush groupings containing less than all of the elements described hereinabove as well as the various permutations thereof are also contemplated by the present invention.

As described herein, the compounds described hereinabove are useful in promoting peptide coupling, i.e., the reaction between a free amino group of a first amino acid or first peptide with a free carboxy group of a second amino acid or peptide. The process of the present invention is general; it can be used in effecting the coupling of two amino acids, a dipeptide and an amino acid, a tripeptide and an amino acid, a tetrapeptide and an amino acid, coupling of one peptide with another peptide, coupling of dipeptides, higher peptides, coupling of polypeptides etc.

When the compound of Formula I reacts with an amino compound such as an amino blocked amino acid or peptide of the formula $BLK_1$—$AA_1$ the corresponding amino acid ester of the formula is formed, i.e.,

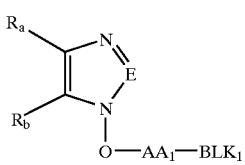

wherein $AA_1$ is an amino acid or peptide as defined herein, $BLK_1$ is an amino blocking group as defined herein and $R_a$, $R_b$ and E are as defined hereinabove. This amino acid ester can then react with a compound having a free amino, such as an arylamino, alkylamino, lower aryl amino, etc. designated as $R_{22}R_{23}NH$, wherein $R_{22}$ and $R_{23}$ are independently hydrogen, lower alkyl, aryl or lower aryl alkyl to form a compound of the formula:

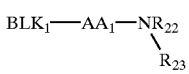

Removal of the blocking group by techniques known to one skilled in the art affords the product:

$AA_1NR_{22}R_{23}$.

This technique is extremely useful when the second amino compound is an amino acid or peptide having a free amine group, designated as AA$_2$. In this case, a peptide is formed between AA$_1$ and AA$_2$; for example,

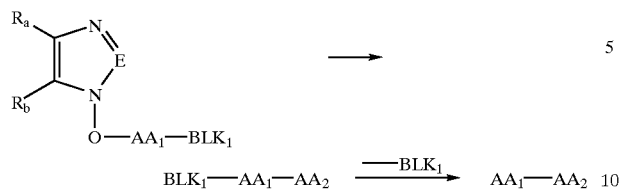

wherein AA$_1$, AA$_2$, BLK$_1$, E, and R$_a$ and R$_b$ are as defined herein.

The blocking group can be any of the blocking groups described herein, but the preferred blocking groups are FMOC, BOC, benzyloxycarbonyl BSMOC and Bspoc.

The term "amino acid" or AA, AA$_1$, or AA$_2$ as used herein refers to an organic acid containing both a basic amino group (NH$_2$) and an acidic carboxyl group. (COOH). Therefore, said molecule is amphoteric and exists in aqueous solution as dipole ions. (See "The Condensed Chemical Dictionary", 10th Ed., edited by Gessner G. Hawley, Van Nostrand Reinhold Company, London, England p. 48 (1981). The preferred amino acids are the α-amino acids. They include but are not limited to the 25 amino acids that have been established as protein constituents. They must contain at least one carboxyl group and one primary or secondary amino group in the amino acid molecule. The term includes such proteinogenic amino acids as alanine, valine, leucine, isoleucine, norleucine, proline, hydroxyproline, phenylalanine, tryptophan, amino isobutryic acid, methionine, glycine, serine, threonine, cysteine, cystine, glutamic acid, lysine, hydroxylysine, ornithine, arginine, histidine, penicillamine, naphthylamine, α-phenylglycine, and the like.

As used herein, the term "peptide" refers to the class of compounds composed of amino acid units chemically bound together with amide linkages. A peptide may contain as little as two amino acid residues or may contain a polymer of amino acid residues (polypeptide).

As used herein, the terms "amino acid" and "peptide" also include amino acids and peptides, respectively containing blocking (protecting) groups. These protecting "groups" block the amino group or the carboxyl group of the amino acid or peptide not involved in or taking part in the coupling in order to prevent unwanted side reactions. These protecting groups also protect reactive groups on the side chain.

A number of blocking reagents for amino groups are known in the art and have been utilized in the syntheses of peptides. These blocking groups are discussed in U.S. Pat. Nos. 3,835,175, 4,508,657, 3,839,396, 4,581,167, 4,394,519, 4,460,501 and 4,108,846, the contents of all of which are incorporated by reference as if fully set forth herein. Other amino protecting groups are discussed in U.S. patent application Ser. No. 364,662, the contents of which are also incorporated by reference. Other amino protecting groups are described in an article entitled "Solid Phase Peptide Synthesis", by G. Barany and R. B. Merrifield in *THE PEPTIDES*, Vol. 2, edited by E. Gross and J. Meienhoffer, Academic Press, N.Y., N.Y. 100–118 (1980), and in the book entitled "PROTECTIVE GROUPS IN ORGANIC SYNTHESIS" by T. W. Green, John Wiley & Sons, New York, the contents of all of which are being incorporated by reference.

The term amino acid protecting group, (BLK, BLK$_1$) as used herein, refers to blocking groups which are known in the art and which have been utilized to block the amino (NH$_2$) group of the amino acid. Blocking groups such as 9-fluorenylmethyloxycarbonyl (FMOC), 2-chloro-1-indanylmethoxycarbonyl (CLIMOC) and benz[f]indene-3-methyloxycarbonyl (BIMOC) and dbd-TMOC are discussed in U.S. Pat. Nos. 3,835,175, 4,508,657, 3,839,396, 4,581, 167, 4,394,519, 4,460,501 and 4,108,846 referred to hereinabove. Moreover, other amino protecting groups such as 2-(t-butyl sulfonyl)-2-propenyloxycarbonyl (Bspoc) and benzothiophene sulfone-2-methoxycarbonyl (Bsmoc) may be utilized. Other N-amino protecting groups include such groups as the t-butyloxycarbonyl (BOC), t-amyloxycarbonyl (Aoc), β-trimethylsilylethyloxycarbonyl (TEOC), adamantyloxycarbonyl (Adoc), 1-methyl-cyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac), o-nitrophenylsulfenyl (Nps), dithiasuccinoyl (Dts), Phthaloyl, piperidinoxycarbonyl, formyl, trifluoroacetyl and the like.

These protecting groups can be placed into four categories:

1) a base labile Nox-amino acid protecting group such as FMOC, and the like.
2) protecting groups removed by acid, such as Boc, TEOC, Aoc, Adoc, Mcb, Bpoc, Azoc, Ddz, Poc, Cbz, 2-furanmethyloxycarbonyl (Foc), p-methoxybenzyloxycarbonyl (Moz), Nps, and the like.
3) protecting groups removed by hydrogenation such as Cbz, and the like.
4) protecting groups removed by nucleophiles, such as Bspoc, Bsmoc, Nps, and Dts, and the like.
5) protecting groups derived from carboxylic acids, such as formyl, acetyl, trifluoroacetyl and the like, which are removed by acid, base or nucleophiles.

A variety of carboxy protecting groups known in the art may be employed. Examples of many of these possible groups may be found in "Protective Groups in Organic Synthesis", by T. W. Green, John Wiley & Sons, 1981, the contents of which are incorporated by reference. These examples include such groups as methyl ester, t-butyl ester, β-trimethylsilylethyl ester, benzyl ester and the like.

In addition, during the course of protein synthesis, it may be necessary to protect certain side chains of the amino acids to prevent unwanted side reactions. The various protecting groups are discussed in U.S. Pat. No. 5,360,928, the contents of which are incorporated herein by reference.

The term "acylating group of an amino acid or peptide" refers to a group on the free carboxy end of the amino acid or peptide that facilitates the acylation reaction, i.e., nucleophilic substitution at the acyl carbon. Examples include the free acid, acid halide, esters, such as lower alkyl esters, phenoxy esters which are unsubstituted or substituted with 1–5 electron withdrawing groups as defined herein; or an anhydride and the like. The preferred acylating derivative is the acid, acid halide, especially the acid chloride or fluoride, and the phenoxy ester.

The preferred acylating amino acid is an amino acid group of the formula

BLK—AA—M, wherein BLK is an amino protecting group

AA is an amino acid and

M is halo or

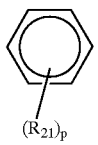

wherein $R_{21}$ is independently halo, lower alkyl, nitro, cyano or other electron withdrawing groups and p is 0–5. When p is 0, the phenoxy ester is unsubstituted.

The most preferred acylating group of an amino acid is the amino acid chloride or fluoride. The preparation and use of amino acid chlorides as an acylating derivative is discussed in an article by Carpino, et al. in *J. Org. Chem.*, 1986, 51, 3734–3736, the contents of which are incorporated herein by reference. Briefly, amino acid chlorides can be prepared by reacting the amino acid with thionyl chloride and recrystallizing the product from a recrystallization reagent, such as $CH_2Cl_2$-hexane.

The preparation and use of amino acid fluorides in peptide synthesis are discussed U.S. Pat. No. 5,360,928, the contents of which are incorporated herein by reference. As described therein, the amino acid fluorides can be prepared by reacting an N-protected amino acid with the reagent cyanuric fluoride. This reaction can be run at temperatures as low as 0° C. and up to the refluxing temperature of the solvent, but it is preferred that the reaction is run at room temperature. It can also be run in an inert solvent, such as pyridine/$CH_2Cl_2$ and the like. The cyanuric fluoride can be prepared from the corresponding chloride in the presence of potassium fluoride at elevated temperatures ranging from 150° to 250° C., according to the following equation

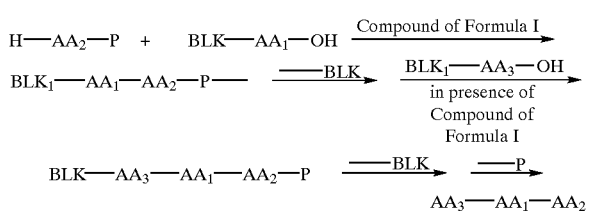

Other fluorinating agents well known in the art, such as thionyl fluoride, 2,4,6-trinitrofluorobenzene, N-methyl-2-fluoropyridinium salts, and the like may be used in place of cyanuric fluoride to give acid fluorides.

A typical preparation of the peptide in accordance with the present invention involves the following steps
1) protection of the free carboxyl group in a first amino acid or a first peptide, unless the amino acid or peptide is anchored to a solid support.
2) protection of the free amino group of a second amino acid or peptide.
3) protection of the side chains, if necessary.
4) coupling the first amino acid or peptide with the second amino acid or peptide in the presence of compounds of Formula I.
5) removal of the protecting groups.

The procedure of steps 1–3 can be performed in any order.

In the coupling step, the compounds of Formula I should be present in effective amounts. Usually, the first amino acid or peptide is present in approximately equimolar amounts with the second amino acid or peptide, although the reaction can take place if the molar ratio of the former to the latter ranges from about 1:3 to about 3:1. Furthermore, the amount of the compound having Formula I used depends upon the amount of peptide or amino acid which is present in the least amount (i.e. the limiting reagent); thus the molar ratio of the compound of Formula I to the amino acid or peptide ranges from about 1:3 to about 3:1 relative to the amino acid or peptide present in the least molar amount, although it is preferred that approximately equimolar amounts of the compound of Formula I, the first amino acid or peptide and the second amino acid or peptide be used.

The coupling reaction usually takes place in an inert organic solvent such as dimethylformamide (DMF) or ethers, such as ethyl ether, THF or dioxane. In fact DMF is the preferred solvent in the solid phase synthesis because of its favorable solvation properties. The reaction takes place under mild conditions usually ranging from about 0° C. to about 30° C. After the peptide is formed, the blocking groups are removed by techniques known to one skilled in the art.

The following sequence is illustrative of the coupling reaction; in the examples below, amino acids (AA) are used, although the procedure is general for amino acids and/or peptides:

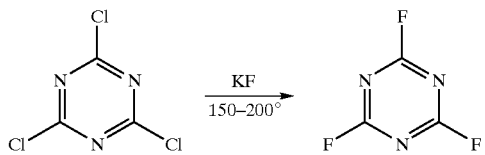

In the above scheme, BLK is an amino acid blocking group, $AA_1$, $AA_2$ and $AA_3$ are first, second and third amino acid, respectively and P is a carboxy protecting group.

As shown by the above scheme, the N-αamino protected amino acid is reacted with a second amino acid in which the carboxy group is protected.

A peptide is formed between the first amino acid and the second amino acid. The peptide chain can be increased by removing the alpha amino protecting group by techniques known to one skilled in the art and then reacting the corresponding dipeptide with another N-α amino protected amino acid in the presence of a compound of Formula I to form the corresponding tri-peptide. The N-α amino protecting group of the tri-peptide is removed and the above-cycle is repeated until the desired peptide has been obtained.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protected group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These methods are well known in the art as discussed in U.S. Pat. Nos. 4,108,846, 3,839,396, 3,835,175, 4,508,657, 4,623,484, 4,575,541, 4,581,167, 4,394,519 as well as in

*Advances in Enzymology*, 32, 221 (1969) and in PEPTIDES, Vol. 2, edited by Erhard Gross and Johannes Meienhoffer, Academic Press, New York pp. 3–255 (1980), the contents of all of which are incorporated herein by reference as if fully set forth herein.

As indicated hereinabove, the present inventors found a means of preparing the O-isomers.

The compounds of the present invention are prepared by reacting the salt,

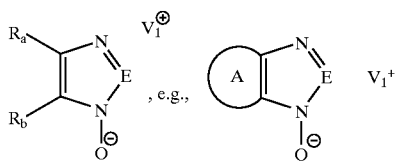

wherein $V_1^+$ is a cation with $R_3Y$ under substitution conditions where Y is a leaving group, such as halide, brosylate, tosylate, and the like and $R_3$ is

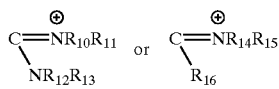

as defined hereinabove. $R_3Y$ has the formula

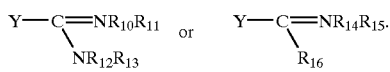

The preferred Y is halide. It is preferable that the reaction is run in an inert polar organic solvent and that the reactants are soluble therein at room temperature and the product is insoluble. Examples of the solvents useful for the synthesis include chloroform, carbon tetrachloride, ethyl ether, dioxane, tetrahydrofuran, methylene chloride and the like. The reaction is conducted at effective temperatures which ranges from the melting point of the solvent to reflux temperatures, but it is preferred that the reaction takes place at about room temperature or slightly elevated temperature, such as up to 60° C.

The inventors found that the presence of any organic base addition to the salt of compound I, even the presence of a weak base, such as triethylamine will produce the N-isomer, and not the O-isomer.

Upon further investigation, the present inventors have found that in the process of preparing the compounds of the present invention, the product that is formed, i.e., the N isomer or the O isomer is dependent upon the interplay of two conflicting factors, thermodynamic stability versus kinetics. More specifically, the inventors have found that the N-isomers are more stable than the O-isomers, but that kinetically the O-isomers are formed faster. Thus, if the above reaction for the formation of the compounds of Formula I described hereinabove were conducted over an extended time, then the O-form would not be isolated, but instead the N-isomer would be isolated. In other words, upon standing the O-isomer product is transformed to the N-isomer form. Consistent with this understanding of the reaction, it is noted that the inventors have not found an instance when the N isomer is transformed to the O-isomer. Thus, to maximize the formation of the O-isomer, the inventors monitor the reaction, either through the formation of the product or the disappearance of the salt or $R_3Y$ and remove the O-isomer therefrom quickly. If conducted in accordance with the reaction procedure described herein, the inventors found that if a stoichiometric molar ratio of salt and $R_3L$, preferably about 1:1 molar ratio is used, than the maximum O-isomer is formed at a time immediately before all of the salt is about to be consumed or immediately after all of the salt is completely reacted. However, if one of the reagents, i.e., the salt of $R_3Y$ is used in a molar excess, than by monitoring the loss of the limiting reagents in the reaction (i.e., whichever reagent on a molar ratio is present in lower amounts) and by stopping the reaction prior to or immediately after the complete consumption of the limiting reagent, the maximum O isomer is produced. Alternatively, the initial product (which is the O-isomer) can be monitored. The present inventors have noted that the N and O isomers have different spectral characteristics which easily allow structural assignment on the basis of IR and $^1H$ and $^{13}C$ NMR analysis and which allow for easily distinguishing the N-isomer and the O-isomer when monitoring the product. Examples are indicated in the table hereinbelow. For example, characteristic IR absorptions for salts derived from tetramethylurea appeared at 1709–1711 and 1664–1675 $cm^{-1}$ for the O- and N-derivatives, respectively. In the $^1H$-NMR spectra thereof, the O-derivatives showed a singlet for the twelve dimethylamino protons near $\delta$ 3.24 whereas the N-compounds showed two singlets for six protons each near $\delta$ 3.0 and 3.4. These differences in the proton NMR spectra agree with expectations based on the effect of hindered rotation in related systems.

TABLE 1

IR, $^1H$- and $^{13}C$-NMR Absorptions for N- and O-HXTU Species[a]

| | Guanidinium Type | | | Uronium Type | | |
|---|---|---|---|---|---|---|
| | IR(cm$^{-1}$) | $^1H$-NMR[b] | $^{13}C$-NMR[c] | | IR(cm$^{-1}$) | $^1H$-NMR[b] | $^{13}C$-NMR[c] |
| N-HATU | 1668.9 | 3.02s, d.37s | 151.9 | O-HATU | 1711.5 | 3.24s | 162.2 |
| N-4-Me-HATU | 1670.4 | 3.02s, 3.48s | 150.1 | O-4-me-HATU | 1711.5 | 3.24s | 162.2 |
| N-4-Cl-HBTU | 1675.6 | 3.00s, 3.44s | 149.3 | O-4-Cl-HBTU | 1711.1 | 3.21s | 161.7 |
| N-HBTU | 1664.4 | 3.02s, 3.37s | 152.7 | O-HBTU | 1709.3 | 3.21s | 162.0 |

[a]IR and NMR data were obtained in $CH_3CN$ and $CD_3CN$, respectively,
[b]Methyl protons,
[c]Cationic carbon atom.

Thus, by taking the spectra of the product formed, the reaction can be monitored. Moreover, the reaction is stopped when the N-isomer product is first noted to be formed and more preferably when no more O-product is seen to be formed. Thus, the maximum O-isomer is formed when no more O-product is formed and the concentration remains constant or is just beginning to decrease. The reaction is stopped by separating the product from the reactants, especially the salt by techniques known in the art, such as filtration, chromatography, crystallization and the like.

The initial time to make the O-isomer is much faster than that of making the N-isomer and is on the order of minutes. In general, the reaction time can be dependent upon the identity of the salt used, the identity of the $R_3Y$, the product formed, the amount of reactants, the solvent system and the like. For example, the reaction time may be as short as 1 minute or 10 minutes. It is preferable that the reaction is conducted for no more than about 1.5 hours, more preferably no more than about 45 minutes and most preferably no more than about 30 minutes and as short as 10 minutes or less.

Armed with this understanding and without wishing to be bound, it is believed that the presence of a base in the reaction described in U.S. Pat. No. 5,644,029, the contents of which are incorporated by reference, drive the reaction to form the more stable product, i.e., the N-isomer.

It is preferred that the product of Formula I is isolated from the reaction mixture and that the isolated product is used for peptide coupling or for forming an amide.

It is also preferred that prior to its use as a coupling agent that the compound of Formula I is substantially pure. The product of Formula I may be purified by techniques known to one of ordinary skill in the art, such as, for example, recrystallization, chromatography, extraction, and the like. It is preferred that the compound of Formula I is at least 80% pure and even more preferably at least 90% pure and most preferably at least about 99% pure.

The N-oxides can be prepared from the compounds of Formula I having a nitrogen ring heteroatom in the heteroaryl or heterocyclic group. These N-oxides are prepared by art recognized techniques by oxidation thereof, such as with peracid, e.g., peracetic acid or n-chloro benzoic acid.

The following non-limiting examples further illustrate the present invention.

EXAMPLE 1
O-hydroxybenzotriazole uronium
1.O-HBTU
(a) KOBt

To a stirred suspension of 1.66 g (12 mmol) of $K_2CO_3$ in 9.5 ml of an aqueous methanol solution (8 ml of MeOH, 1.5 ml of $H_2O$) was added 2.03 g (15 mmol) of HOBt at room temperature. Carbon dioxide gas was evolved immediately, and the mixture was stirred overnight at room temperature. Excess $K_2CO_3$ was filtered and removal of solvent in vacuo gave a white solid, which was recrystallized twice by solution in MeOH followed by precipitation with $Et_2O$ to give 2.31 g (89%) of the potassium salt as a white solid. The crude solid was used as such.

(b) O-HBTU

To a suspension of 0.26 g (1.3 mmol) of KOBt in 15 ml of acetonitrile was added 0.42 g (1.3 mmol) of tetramethylchloroformamidinium hexafluorophosphate ("TCFH") at room temperature. The suspension was stirred for 1 min at room temperature, and the insoluble white solid was filtered immediately. To the filtrate, 100 ml of anhydrous ether was added quickly to give a white precipitate. The white solid was filtered at once to give 0.40 g (79%) of a mixture of the N-(IR ($CH_3CN$): 1662 $cm^{-1}$) and O-form (IR ($CH_3CN$): 1709 $cm^{-1}$) of HBTU. To the mixture, 50 ml of $CH_2Cl_2$ was added and filtration gave 0.11 g (22%) of the N-form, the properties of which agreed with those of commercial HBTU. Addition of ether to the filtrate gave 0.25 g (51%) of nearly pure O-form (IR shows no absorption at 1662 $cm^{-1}$ which is a characteristic of the N-form). Recrystallization by solution in $CH_2Cl_2$ followed by precipitation with $Et_2O$ gave 0.14 g (28%) of O-HBTU: m.p. 118–120° C.; $^1$H NMR (200 MHz, $CD_3CN$) δ 8.16 (d, 1, Ar), 7.80 (m, 2, Ar), 7.61 (m, 1, Ar). 3.20 (s, 12, C(N($CH_3$)$_2$)$_2$); IR ($CH_3CN$) 1709.3 $cm^{-1}$. Anal. Calcd. For $C_{11}H_{16}N_5OPF_6$: C, 34.84; H 4.22; N, 18.47. Found: C, 34.98; H, 4.24; N, 18.65. The product was confirmed by x-ray crystallography.

EXAMPLE 2
O-HATU (O-HYDROXYAZABENZOTRIAZOLE URONIUM)
1.KOAt

KOAt was obtained according to the method described above for KOBt from 2.04 g (15 mmol) of HOAt and 1.66 g (12 mmol) of $K_2CO_3$. Recrystallization twice by solution in MeOH followed by precipitation with $Et_2O$ gave 2.31 g (89%) of the potassium salt as a white solid. The crude solid was used as such.

2. O-HATU

To suspension of 0.26 g (1.3 mmol) of KOAt (potassium salt of 1-hydroxy-7-azabenzotriazole) in 15 ml of acetonitrile was added to 0.42 g (1.3 mmol) of TCFH at room temperature. The suspension was stirred for 2 min at room temperature, and the insoluble white solid (0.09 g) was filtered. To the filtrate, 100 ml of anhydrous ether was added which gave a white precipitate immediately. The white solid was filtered at once to give 0.425 g (86%) of mixed N-(IR($CH_3CN$): 1668.9 $cm^{-1}$) and O-forms (IR($CH_3CN$): 1711.5 $cm^{-1}$) of HATU. To the mixture, 50 ml of $CH_2Cl_2$ was added and filtration gave 0.20 g (22%) of a mixture of the same two forms according to IR analysis. Addition of ether to the filtrate gave 0.25 g (51%) of nearly pure O-form (IR shows no absorption of 1668.9 $cm^{-1}$ which is characteristic of the N-form). Recrystallization by solution in $CH_2Cl_2$ followed by precipitation with $Et_2O$ gave 0.11 g (22%) of O-HATU:m.p. 143–147° C.; $^1$H NMR (200 MHz, $CD_3CN$) δ 8.82 (dd, 1, Pyr), 8.86 (dd, 1, Pyr), 7.65 (dd, 1, Pyr), 3.24 (s, 12, C(N($CH_3$)$_2$)$_2$); IR ($CH_3CN$): 1711.5 $cm^{-1}$. From the filtrate an additional 0.155 g (31%) of the O-form was recovered, making the total yield 0.265 g (54%). Anal. Calcd. For $C_{10}H_{15}N_6OPF_6$: C. 31.58; H, 3.95: N, 22.11. Found: C, 31.39: H, 3.80; N, 22.17. The product was confirmed by x-ray crystallography.

EXAMPLE 3
1. Synthesis of O-HBTU

This was prepared on a large scale as follows:

KOBt (0.5 mol) in 100 ml of water was added to a solution of TCFH (0.5 mol) in 1.5 L of methylene dichloride with vigorous stirring at room temperature. The reaction mixture was stirred at room temperature for 1 min and the organic layer collected. Alternatively the mixture can be filtered through anhydrous magnesium sulfate using a water aspirator. The organic layer was washed with three 150 ml portions of water and dried over magnesium sulfate. The solvent was removed in vacuo and the solid recrystallized from ether to give 113.3 g (59.8%) of pure O-HBTU.

The pure N-HBTU was obtained by washing the magnesium sulfate residue with two 200 ml portions of acetonitrile, removing the solvent in vacuo and recrystallizing from acetonitrile/ether to give 59.8 g (31.6%) of pure N-HBTU. The total yield was 91.4%.

If NMR analysis showed that the O-HBTU is contaminated by starting TCFH (in some cases about 5% TCFH was found), it can be removed by dissolving in methylene dichloride and washing with water (3×150 ml) or by adding 150–200 ml of water and stirring at room temperature for 3 to 4 min, filtering, washing with ether and recrystallizing from methylene dichloride/ether to give the pure O-HBTU.

EXAMPLE 4

Synthesis of O-HATU

The procedure of Example 3 was used to prepare O-HATU except that the reaction mixture was stirred for 5–10 min instead of 1 min. and that KOAt was used instead of KOBt. In this case, there was no contamination by the N-isomer. The yield of pure O-HATU was 78.9%.

EXAMPLE 5

O-HAPyU 10 mM KOAt, 200 ml $CH_2Cl_2$, 50 ml $CH_3CN$ and 10 mmoles of bis(tetramethylene)chloroformamidinum hexafluorophosphate (BP) were stirred at room temperature for two minutes. A precipitate formed and the solid was filtered immediately and collected. The O-product was collected. To the filtrate, 100 ml of anhydrous ether was added and a white precipitate was formed, which was recrystallized by dissolving in the minimum amount of $CH_2Cl_2$ and adding excess ether. The yield of the O-isomer of HAPyU was 73.2%.

The first precipitate was a mixture of 1.3 g of both the N and O forms, the second precipitate contained 1.2 grams of the O-form. The O-form in the IR exhibits an absorption at 1685 $cm^{-1}$. The N-isomer exhibits the IR absorption at 1655 $cm^{-1}$. NMR ($CD_3CN$) δ1.99 (m, 8H), 3.8 (m, 8H), 7.63 (dd, 1H), 8.5 (d, 1H), 8.8 (d, 1H).

The following example is directed to the 4,5-benzo derivative of an uronium cation viz., N-(dimethylamino) (3H-1,2,3-triazolo-[4,5-c] isoquinolin-3-yloxy)-N-methyl-methaminium hexafluorophosphate [4,5-B(HATU)].

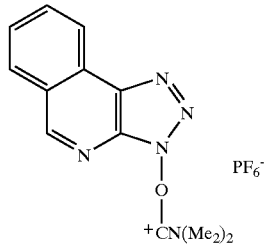

EXAMPLE 6

N-[dimethylamino)(3H-1,2,3-triazolo-[4,5-c] isoquinolin-3-yl-oxy)-N-methylmethanaminium haxafluorophosphate A. 1-H-1-Hydroxy-2-azanaptho[3,4-d]-triazole

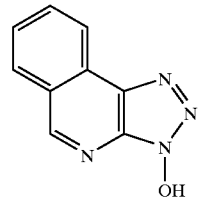

A. 1H-1-Hydroxy-2-azanaphtho[3,4-d]-triazole
1. Isoquinoline-N-oxide
To a solution of isoquinoline (76.93 g, 595.6 mmol) in acetic acid (520 mL) was added portionwise every 10 min. 33.6 g of sodium perborate, $NaBO_3.4H_2O$. Over a 1 hour period a total of 201.6 g (1.31 mole) of perborate was added. The resulting mixture was stirred at 60° C. for 24 hours after which acetic acid was removed by passing a stream of air over the surface of the liquid contained in a large flat vessel overnight. The remaining solid was dissolved in 1 L of water and the solution neutralized with solid sodium bicarbonate. The solution was extracted with chloroform (3×300 mL) and the organic extracts dried over magnesium sulfate. Chloroform was evaporated and the residual white solid was redissolved in chloroform and precipitated by addition of hexane to give 65 g (75%) of the N-oxide: mp 138–140° C. (lit mp 141–142° C.)
2. 4-Hydroxyisoquinoline
To a solution of isoquinoline-N-oxide (7.93 g, 54.63 mmol) in chloroform (160 mL) was added portionwise p-toluenesulfonyl chloride (19.66 g, 103.1 mmol). After the mixture had been refluxed for one hour solvent was removed with a rotary evaporator, and the dense solution was dissolved in methanol (100 mL). After a few minutes, a white solid precipitated. After standing overnight filtration gave 4.8 g (60.4%) of the hydroxy compound, mp 223–224° C.
3. 3-Nitro-4-hydroxyisoquinoline
To a solution of 3 g (20.6 mmol) of 4-hydrocyisoquinoline dissolved in 14 mL of conc. $H_2SO_4$ there was added 2.4 g of $KNO_3$ during 30 min. while keeping the temperature between 50–55° C. The mixture was maintained at this temperature for 3 hours after which the reaction mixture was poured onto crushed ice. The yellow precipitate was collected, washed with water and recrystallized from ethanol to give 1.43 g (36.4%) of the nitroquinoline as yellow needles: mp 170–171° C. (lit mp 173° C.); $^1$H-NMR (DMSO-$d_6$ 200 MHz) δ 8.80 (s, 1H), 8.64 (d, 1H), 8.36 (d, 1H), 8.0 (dd, 1H), 7.61 (dd, 1H); IR (KBr) 2408 (broad, OH), 1569 (s, $NO_2$), 1488 (s, $NO_2$) $cm^{-1}$
4. 3-nitro-4-chloroisoquinoline
To 13.25 g (69.7 mmol) of 4-hydroxy-3-nitroisoquinoline was added 120 mL of phosphorous trichloride. After the mixture had been refluxed for 3 hours, 80 mL of $POCl_3$ was distilled out. The remaining solution was poured onto approximately 150 g of crushed ice. The resulting solid was filtered and recrystallized from ethanol to give 6.2 g (42.5%) of the chioroquinoline as yellow needles: mp 103–104° C. (lit mp 108–109° C.); 1H-NMR (DMSO-$d_6$, 200 MHz) δ 9.20 (s, 1H), 8.5 (d, 1H) 8.30 (d, 1H), 7.8 (m, 2H); IR (KBr) 1530 (s, $NO_2$), 1344 (s, $NO_2$) $cm^{-1}$.

5.1 H-1-Hydroxy-2-azanaphtho[3,4-d]-triazole

A solution of 4-chloro-3-nitroisoquinoline in ethanol (120 mL) was preheated to 40° C. and 9.8 mL of anhydrous hydrazine was added. The mixture was refluxed for 3 hours, the solvent evaporated by means of a rotary evaporator and the residual yellow solid dissolved in 600 mL of water. The mixture was filtered and the filtrate acidified by addition of concentrated HCl. The resulting brown solid was filtered and recrystallized from boiling water in the presence of decolorizing carbon to give 2 g (37.3%) of the hydroxy triazole as pale yellow crystals: mp 245° C. (dec); $H^1$ NMR (DMSO-$d_6$, 200 MHz) δ 9.39 (s, 1, 1H) 8.59 (4, 1, 2H), 8.41 (d, 1, 4H), 8.08 (dd, 1, 4H), 7.85 (dd. 1, 5H) $J_{4,5}$ 8.15 Hz, $J_{2,3}$ 8.11 Hz; IR (KBr), 2493 (broad, OH), 1445 (s), $cm^{-1}$.

Anal Calcd for $C_9H_6 N_4O$: C, 58.06; H 3.25; N, 30.09. Found: C, 58.08; H, 3.30; N, 30.20.

B. N-[dimethylamino)(3H-1,2,3-triazolo-[4,5-c]isoquinolin-3-yl-oxy)-N-methylmethanaminium haxafluorophosphate Under an atmosphere of dry $N_2$ 1.0 mL of triethylamine was added to a suspension of the product of A-5 (1.22 g, 6.57 mmol) in 60 mL of dry $CH_2Cl_2$. After stirring for 5 minutes at room temperature, the resulting light yellow solution was cooled to 0° C. and 1.84 g (6.57 mmol) of TCHF was added in one portion. The mixture was stirred for 30 num at 0° C. and then for 3 hours at room temperature. The precipitate was collected and washed with methylene chloride. The white solid was recrystallized from $CH_3CN$/ether to give 1.55 (55%) of pure uronium salt: mp 187–191° C. (dec) $^1$H-NMR ($CD_3CN$, 200 MHz) δ 9.37 (s, 1H), 8.69 (d, 1H), 8.41 (d, 1H), 8.10 (dd, 1H), 7.91 (dd, 1H), 3.30 (s, 12H, —$CH_3$). IR ($CH_3CN$) 1712 (s, CN), 1625 (w), 1585 (w) $cm^{-1}$.

Anal. Calcd. for $C_{14}H_{17}N_6OPF_6$: C,39.08; H,3.98; N, 19.53. Found: C, 39.14; H, 4.02; N, 19.37.

The present inventors have found that the rate of forming peptides is significantly faster using the O-isomer relative to the corresponding N-isomer. During peptide coupling, it is also preferred that the reaction is monitored, since some of O-isomer may isomerize to the N-isomer. However, inasmuch as the coupling reaction with the O-isomer is significantly faster than with the N-isomer, the formation of the N-isomer during the coupling reaction is minimized.

Moreover, the present inventors have found that higher yields of product are formed with the O-isomers than with the corresponding N-isomers. In addition, the inventors have found that higher yields of peptide occurs when the compounds of Formula II are used especially wherein A in Formula II is heteroaryl, particularly 1-pyridyl, than when A is aryl, e.g., phenyl. Moreover, less epimerization occurs when using the O-isomer then when the using corresponding N-isomer in the coupling reaction.

These findings are illustrated in the following examples.

EXAMPLE 7

Z-Phe-Val-OH was coupled with HPro-$NH_2$ in the presence of base and the coupling reagent listed in the table in DMF, as indicated hereinbelow and the extent of loss of configuration at valine was determined. The results are given hereinbelow.

$$\text{Z-Phe-Val-OH} \xrightarrow[\text{B/CR/DMF}]{\text{H-Pro-NH}_2} \text{Z-Phe-Val-Pro-NH}_2$$

Extent of Loss Configuration at Valine:

| Coupling Reagent | Base | LDL-(%) |
|---|---|---|
| O-HAPyU | TMP* | 2.8 |
| N-HAPyU | TMP | 3.3 |
| O-HATU | TMP-DIEA**(1:1) | 3.4 |
| N-HATU | TMP-DIEA(1:1) | 5.9 |
| O-HBTU | TMP-DIEA(1:1) | 10.3 |
| N-HBTU | TMP-DIEA(1:1) | 20.6 |

*TMP is 2,4,6-trimethylpyridine
**DIEA is diisopropylethylamine
***Z is benzyloxycarbonyl

EXAMPLE 8

The procedure of Example 7 was repeated except that Z-Gly-Phe-OH was used to couple with the H-Pro-$NH_2$ according to the following equation:

$$\text{Z-Gly-Phe-OH} \xrightarrow[\text{B/CR/DMF}]{\text{H-Pro-NH}_2} \text{Z-Gly-Phe-Pro-NH}_2$$

| Coupling Reagent | Base | LDL-(%) |
|---|---|---|
| O-HATU | TMP | 0.36 |
| N-HATU | TMP | 0.75 |

Again, with the O-isomer, there was significantly less epimerization than when using the N-isomer.

Moreover, as shown hereinbelow, amino acid activation occurs more quickly in the presence of the O-isomer than the N-isomer.

EXAMPLE 9

In this example, Z-Aib-OH (carbobenzyloxyamino isobutyric acid) was reacted with HATU or HBTU in the presence of a base and the half life for formation of the product was measured.

| Coupling Reagent | Half life ($t_{1/2}$) |
|---|---|
| (a) one equivalent TMP | |
| O-HATU | <2 min |
| N-HATU | ~7 min |
| O-HBTU | >1 hour (40% ester at this point) |
| N-HBTU | >1 hour (28.9% ester at this point) |
| (b) two equivalents TMP | |
| O-HATU | <2 min |
| N-HATU | <2 min |
| O-HBTU | ~4 min |
| N-HBTU | ~90 min |

As clearly shown, amino acid activation using the O-isomer proceeded more rapidly than for the corresponding N-isomer. Thus, Z-Aib-OH was converted to Z-Aib-OAt in the presence of one equivalent of collidine with a half life of less than 2 minutes with O-HATU, whereas for N-HATU, under the same conditions, $t_{1/2}$ was about 7 minutes. For HBTU, $t_{1/2}$ was less than 1 hour for both O (40% OBt ester at 1 hour) and N-isomers (29% OBt ester at 1 hour); however, significantly more O-ester was formed than N-ester. Moreover, if two equivalents of TMP were used the half lives of O-HBTU and N-HBTU are markedly different, the former being 4 minutes and the latter being 90 minutes.

EXAMPLE 10
Assembly of ACP Decapeptide
H-Val-Gln-Ala-Ala-Ile-Asp-Tyr-Ile-Asn-Gly-NH$_2$ (SEQ ID NO: 1)

Test peptides were assembled on a PAL-PEG-PS resin (0.18 mmol/g) by the solid phase method manually in DMF with DIEA or DIEA/TMP (1:1) as base. For ACP the so-called "1.5×1.5" method described by Carpino, et al. in J. Chem. Soc., Chem Comm (1994), the contents of which are incorporated by reference, was used. This involved the protected amino acid and coupling reagent taken as 1.5 equivs. with 3 equivs. of the base in DMF (conc. 0.2–0.3 M). The acid and coupling reagent were mixed together for 30 sec or 7 min and the solution was then added to the resin and the mixture was allowed to stand with occasional stirring by means of a teflon spatula for 1.5 min. The resin was washed with DMF (3×5 ml), deblocked with 20% piperidine in DMF for 7 min, washed with DMF, CH$_2$Cl$_2$ and DMF, respectively (3×5 ml each). Each amino acid was added similarly. The final deblocking was carried out with TFA/H$_2$0 (9:1) for 2 h at room temperature. TFA was removed in vacuo and the peptide precipitated with anhydrous ether. HPLC conditions involved a gradient of 5 to 35% acetonitrile in 0.1% TFA over 25 min. Automated syntheses involved standard instrument protocols.

The results are as follows:

| Coupling Reagent* | % Yield ACP |
| --- | --- |
| N-HBTU | 51.8% |
| O-HBTU | 78.1% |
| N-HATU | 89.4% |
| O-HATU | 91.6% |

*Conditions 2-fold excess AA; 10–30 sec preactivation, 2 fold excess TMP/DIEA (1:1), 1.5 min coupling

EXAMPLE 11

The procedure is the same as that of Example 10 except the excess AA was 1.5 eq. The results are as follows:

| Coupling Reagent | % Yield ACP |
| --- | --- |
| N-HATU | 66.4% |
| O-HATU | 81.2% |

EXAMPLE 12
Aib-Aib Analog of Leucine Enkephelin
H-Tyr-Aib-Aib-Phe-Leu-NH$_2$ (SEQ ID NO: 2)

For the Aib-Aib 5-mer standard syntheses were carried out on the ABI instrument using 1.5 equivs of protected amino acid and 3.5 min coupling time. With HBTU as a coupling reagent, the major product is expected to be, as observed with 30-sec preactivation, the pentapeptide. However, a second peptide the des-Aib tetrapeptide was also formed. For longer preactivation times, e.g., 7 min., a significant amount of the resulting product lacks both Aib units.

The test results are as follows:

| Coupling Reagent* | % of des-Alb tetrapeptide | % of pentapeptide |
| --- | --- | --- |
| N-HBTU | 48% | 52% |
| O-HBTU | 38% | 62% |

*Conditions 4 fold excess AA, 8-fold excess DIEA, 30–60 sec preactivation, 30 min coupling.

Thus, there was more desired peptide formed using O-HBTU than N-HBTU.

Without wishing to be bound, it is believed that the proportion of O-acyl species formed is greater when the O-isomer is reacted with an amino acid or peptide than with the corresponding N-isomer and that this leads to greater reactivity in the formation of amides, e.g., peptides.

Infrared examination of the activation process for the triazole derivative (when E=N) shows that the O-form is generated rapidly with subsequent isomerization to the N-form occurring more or less rapidly depending on the nature of the system and/or solvent. Since the O-acyl form is more reactive, such effects may be one factor in rationalizing the greater efficiency of carrying out peptide assembly under conditions of "low preactivation".

A connection can be established between the two varieties of species since HPLC analysis allows separation of the O- and N-acyl derivatives, such as

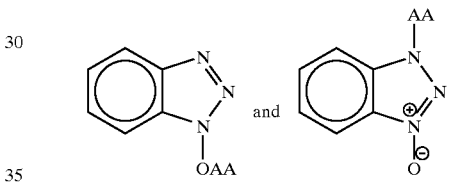

for a number of simple amino acids such as Fmoc-Val-OH. Thus treatment of this amino acid with O-HBTU in the presence of 1 eq of DIEA shows that after 2 min the major species present is the O-acyl ester (ratio O—/N— 99.5/0.5). After 15 min the ratio has changed to 88/12. For N-HBTU the O—/N— ratio at 2 min is 87.9/12.1 suggesting a clear relationship between the structure of the coupling reagent and that of the initial activated species. Since the major extent of acylation occurs in the first few minutes of reaction time, this can explain both the higher effectiveness of authentic uronium salts (O-isomer) and the so-called low preactivation procedure.

As used herein, the 4-position is the position on the ring fused to the diazole or triazole and which is α to the bridgehead which is on the opposite side of the ring to the nitrogen atom substituted by OR$_3$. It is at least 3 ring atoms from the nitrogen atom substituted by OR$_3$. For example, in the structure

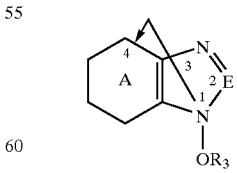

the 4-position is as indicated. It is 3 ring carbon atoms from the nitrogen containing the OR$^3$ group if the ring atoms are counted in the direction of the arrow.

As used herein, the singular denotes the plural and vice versa.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A salt, wherein the cationic portion has the formula

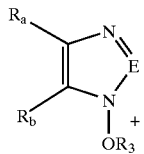

wherein $R_3$ is a positively charged electron withdrawing group having the formula:

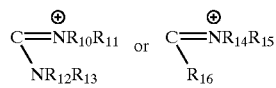

$R_{10}$, $R_{11}$, $R_{12}$, $R_{13}$, $R_{14}$, $R_{15}$, $R_{16}$ are independently hydrogen or lower alkyl which may be unsubstituted or substituted with an electron withdrawing or electron donating group, or $R_{10}$ and $R_{12}$ taken together with the nitrogen atom to which they are attached and the carbon atom attached to the nitrogen atoms form a 5 or 6 membered nitrogen containing heterocyclic containing 3 or 4 ring carbon atoms, respectively or $R_{10}$ and $R_{11}$ taken together with the nitrogen atom to which they are attached or $R_{12}$ and $R_{13}$ taken together with the nitrogen atom to which they are attached form a 5 or 6-membered heterocyclic ring containing up to 5 ring carbon atoms respectively or $R_{14}$ and $R_{15}$ taken together with the nitrogen atom to which they are attached form a 5 or 6-membered heterocyclic ring containing 4 or 5 ring carbon atoms, respectively or $R_{14}$ taken together with the nitrogen to which it is attached and $R_{16}$ taken together with the carbon atoms attached thereto form a 5 or 6 membered nitrogen containing heterocyclic ring, containing 4 or 5 ring carbon atoms, respectively;

E is N or CR;

R is hydrogen or lower alkyl;

$R_a$ and $R_b$ taken together with the carbon atoms to which they are attached form a an oxygen, sulfur or nitrogen heterocyclic group wherein said heterocyclic group contains from 3 up to a total of 14 ring atoms and from 3 up to a total of 13 ring carbon atoms, and up to a total of 20 carbon atoms, said ring containing at least 1 heteroatom ring atom, said heteroatom present on the ring being selected from the group consisting of N, O, and S, a nitrogen, oxygen or sulfur heteroaryl group wherein said heteroaryl ring is an oxygen, sulfur, or nitrogen containing heteroaromatic ring containing 5 to 14 ring atoms and up to a total of 4 to 13 ring carbon atoms and 20 carbon atoms, said heteroatom being selected from the group consisting of N, O, and S, which heterocyclic, and heteroaryl groups are unsubstituted or substituted by lower alkyl, an electron withdrawing group or an electron donating group.

2. The salt according to claim 1 wherein E is CH or N.

3. The salt according to claim 1 wherein $R_3$ is

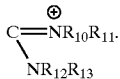

4. The salt according to claim 3 wherein $R_{10}$, $R_{11}$, $R_{12}$ and $R_{13}$ are independently hydrogen or lower alkyl which may be unsubstituted or substituted with an electron donating group.

5. The salt according to claim 4 wherein the electron donating group is lower alkoxy.

6. The salt according to claim 5 wherein $R_{10}$, $R_{11}$, $R_{12}$ and $R_{13}$ are independently methyl, ethyl, propyl, butyl, pentyl or $CH_2CH_2OCH_2CH_3$.

7. The salt according to claim 1 wherein $R_{10}$, $R_{11}$, $R_{12}$ and $R_{13}$ are the same.

8. The salt according to claim 1 wherein $R_3$ is

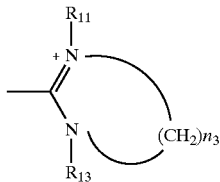

wherein $R_{11}$ and $R_{13}$ are independently hydrogen or lower alkyl, which may be unsubstituted or substituted with electron donating group or electron withdrawing groups, and $n_3$ is 2 or 3.

9. The salt according to claim 8 wherein $R_{11}$ and $R_{13}$ are independently hydrogen or unsubstituted lower alkyl.

10. The salt according to claim 9 wherein $R_{11}$ and $R_{13}$ are independently hydrogen or methyl.

11. The salt according to claim 1 wherein $R_3$ is

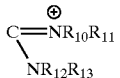

wherein $R_{10}$ and $R_{11}$ taken together with the nitrogen atom to which they are attached form a 5 or 6 membered nitrogen containing heterocyclic ring containing up to 5 carbon ring atoms; and $R_{12}$ and $R_{13}$ are independently hydrogen or lower alkyl which may be unsubstituted or substituted with an electron withdrawing or electron donating group or $R_{12}$ and $R_{13}$ taken together with the nitrogen atom to which they are attached form a 5 or 6 membered nitrogen containing heterocyclic ring containing up to 5 carbon ring atoms.

12. The salt according to claim 11 wherein $R_3$ is

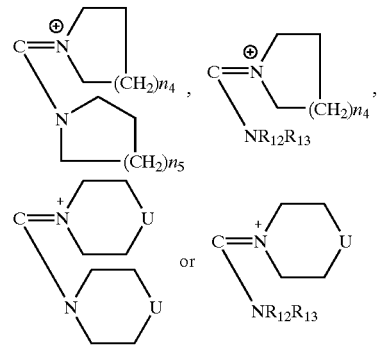

wherein
U is N-ALK, $CH_2$ or O;
ALK is lower alkyl or hydrogen;
$n_4$ and $n_5$ are independently 1 or 2; and
$R_{12}$ and $R_{13}$ are independently hydrogen or lower alkyl.

13. The salt according to claim 12 wherein $R_3$ is

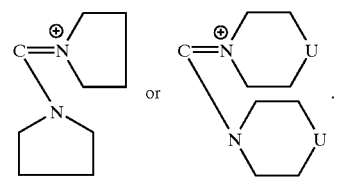

14. The salt according to claim 1 wherein $R_a$ and $R_b$ taken together is heterocyclic.

15. The salt according to claim 1 wherein $R_a$ and $R_b$ taken together is unsubstituted heterocyclic, or unsubstituted heteroaryl.

16. A salt, wherein the cation has the formula:

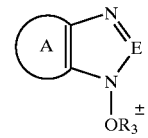

or N-oxides thereof wherein

A is a heteroaryl ring wherein said heteroaryl ring is an oxygen, sulfur or nitrogen containing heteroaromatic having from 5 up to a total of 14 ring atoms and from 3 up to a total of 13 ring carbon atoms, and up to a total of 20 carbon atoms; said heteroaryl and aryl groups may be unsubstituted or substituted with an electron donating, an electron withdrawing group or lower alkyl;

E is CR or N;

R is H or lower alkyl $R_3$ is a positively charged electron withdrawing group having the formula:

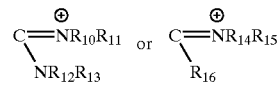

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing heterocyclic ring containing up to a total of 5 carbon ring atoms.

17. The salt according to claim 16 wherein E is CH or N.

18. The salt according to claim 16 wherein $R_3$ is $$C=\overset{\oplus}{N}R_{10}R_{11}.$$
$$\quad\ \ \backslash NR_{12}R_{13}$$

19. The salt according to claim 18 wherein $R_{10}$, $R_{11}$, $R_{12}$ and $R_{13}$ are independently hydrogen or lower alkyl which may be unsubstituted or substituted with an electron donating group.

20. The salt according to claim 19 wherein the electron donating group is lower alkoxy.

21. The salt according to claim 20 wherein $R_{10}$, $R_{11}$, $R_{12}$ and $R_{13}$ are independently methyl, ethyl, propyl, butyl, pentyl or $CH_2CH_2OCH_2CH_3$.

22. The salt according to claim 16 wherein $R_{10}$, $R_{11}$, $R_{12}$ and $R_{13}$ are the same.

23. The salt according to claim 16 wherein $R_3$ is

[structure with $R_{11}$, $+N$, $N$, $R_{13}$, $(CH_2)n_3$]

wherein $R_{11}$ and $R_{13}$ are independently hydrogen or lower alkyl, which may be unsubstituted or substituted with electron donating group or electron withdrawing groups, and $n_3$ is 2 or 3.

24. The salt according to claim 23 wherein $R_{11}$ and $R_{13}$ are independently hydrogen or unsubstituted lower alkyl.

25. The salt according to claim 24 wherein $R_{11}$ and $R_{13}$ are independently hydrogen or methyl.

26. The salt according to claim 16 wherein $R_3$ is $$C=\overset{\oplus}{N}R_{10}R_{11}$$
$$\quad\ \ \backslash NR_{12}R_{13}$$

wherein $R_{10}$ and $R_{11}$ taken together with the nitrogen atom to which they are attached form a 5 or 6 membered nitrogen containing heterocyclic ring containing up to 5 carbon ring atoms; and $R_{12}$ and $R_{13}$ are independently hydrogen or lower alkyl which may be unsubstituted or substituted with an electron withdrawing or electron donating group or $R_{12}$ and $R_{13}$ taken together with the nitrogen atom to which they are attached form a 5 or 6 membered nitrogen containing heterocyclic ring containing up to 5 carbon ring atoms.

27. The salt according to claim 26 wherein $R_3$ is

[four cyclic structures with $(CH_2)n_4$, $(CH_2)n_5$, $NR_{12}R_{13}$, U]

or wherein

U is N-ALK, $CH_2$ or O;

ALK is lower alkyl or hydrogen;

$n_4$ and $n_5$ are independently 1 or 2; and $R_{12}$ and $R_{13}$ are independently hydrogen or lower alkyl.

28. The salt according to claim 16 wherein $R_3$ is

[two cyclic structures with U]

or

29. The salt according to claim 16 wherein A is unsubstituted.

30. The salt according to claim 1 wherein the cation has the formula:

[bicyclic heterocyclic structure with G, J, L, M, E, N, $OR_3$]

wherein

G is N or $CR_1$;

J is N or $CR_2$;

L is N or $CR_8$;

M is N or $CR_5$;

$R_2$, $R_8$ and $R_5$ are independently hydrogen or lower alkyl which may be unsubstituted or substituted with an electron donating group or electron withdrawing group;

$R_1$ is hydrogen;

E is N or CR;

R is hydrogen or lower alkyl;

$R_3$ is a positively charged electron withdrawing group having the formula:

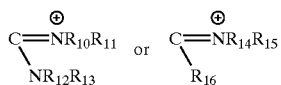

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing heterocyclic ring containing up to a total of 5 carbon ring atoms.

31. The salt according to claim 30 wherein J, L and M are either N or CH, wherein at most two of G, J, L or M is N.

32. The salt according to claim 30 wherein the cation has the formula:

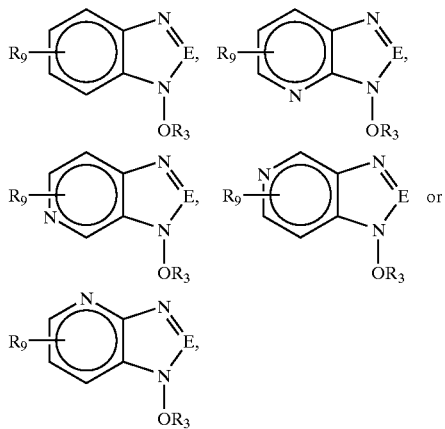

wherein $R_9$ is hydrogen, lower alkyl or electron donating or electron withdrawing group.

33. The salt according to claim 32 wherein the cation has the formula:

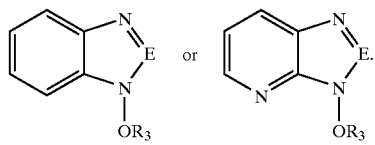

34. The salt according to claim 1 wherein the cation has the formula:

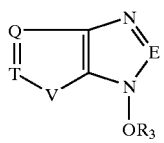

wherein

V is O, S or NH;
Q is N or $CR_6$;
T is N or $CR_7$;
E is CR or N;
R is hydrogen or lower alkyl;
$R_6$, $R_7$ and $R_8$ are independently hydrogen or lower alkyl which may be unsubstituted or substituted with an electron donating group or electron withdrawing group;
$R_3$ is a positively charged electron withdrawing group having the formula:

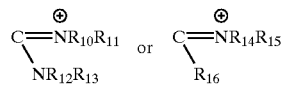

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing heterocyclic ring containing up to a total of 5 carbon ring atoms.

35. The salt according to claim 34 wherein Q is $CR_6$ and T is $CR_7$.

36. The salt according to claim 35 wherein $R_6$ and $R_7$ are hydrogen.

37. The salt according to claim 34 wherein one of Q and T is N.

38. The salt according to claim 1 wherein the cation has the formula:

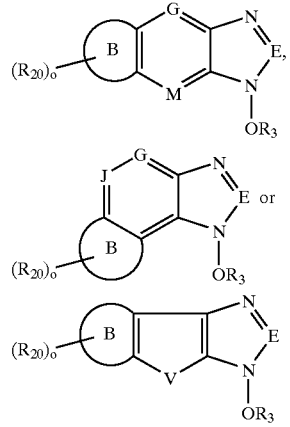

wherein B is an aromatic ring having 6 to 10 ring carbon atoms or a heteroaryl ring having 6 to 10 ring atoms and up to 3 ring heteroatoms and up to a total of 9 ring carbon atoms, which B group may be unsubstituted or substituted with lower alkyl, or electron donating group or electron withdrawing group;

E is CR or N;

$R_3$ is a positively charged electron withdrawing group having the formula:

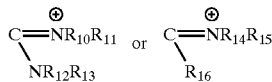

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing hetero cyclic ring containing up to a total of 5 carbon ring atoms;

G is N or $CR_1$;

M is N or $CR_5$;

J is N or $CR_2$;

V is O, S or NH;

$R_1$ is hydrogen;

$R_2$ and $R_5$ are independently hydrogen or lower alkyl, which may be unsubstituted or substituted with an electron donating group or electron withdrawing group.

39. The salt according to claim 38 wherein E is N or CH.

40. The salt according to claim 39 wherein E is N.

41. The salt according to claim 16 wherein the cation has the formula:

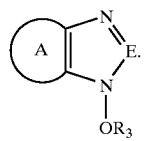

42. The salt according to claim 41 wherein $R_3$ is

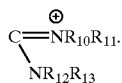

43. The salt according to claim 42 wherein $R_{10}$, $R_{11}$, $R_{12}$ and $R_{13}$ are independently hydrogen or lower alkyl which may be unsubstituted or substituted with an electron donating group.

44. The salt according to claim 43 wherein the electron donating group is lower alkoxy.

45. The salt according to claim 42 wherein $R_{10}$, $R_{11}$, $R_{12}$ and $R_{13}$ are independently methyl, ethyl, propyl, butyl, pentyl or $CH_2CH_2OCH_2CH_3$.

46. The salt according to claim 42 wherein $R_3$ is

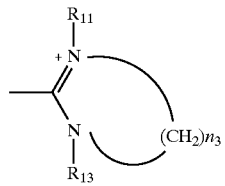

wherein $R_{11}$ and $R_{13}$ are independently hydrogen or lower alkyl, which may be unsubstituted or substituted with electron donating group or electron withdrawing groups, and $n_3$ is 2 or 3.

47. The salt according to claim 46 wherein $R_{11}$ and $R_{13}$ are independently hydrogen or unsubstituted lower alkyl.

48. The salt according to claim 46 wherein $R_{11}$ and $R_{13}$ are independently hydrogen or methyl.

49. The salt according to claim 42 wherein $R_3$ is

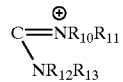

wherein $R_{10}$ and $R_{11}$ taken together with the nitrogen atom to which they are attached form a 5 or 6 membered nitrogen containing heterocyclic ring containing up to 5 carbon ring atoms; and $R_{12}$ and $R_{13}$ are independently hydrogen or lower alkyl which may be unsubstituted or substituted with an electron withdrawing or electron donating group or $R_{12}$ and $R_{13}$ taken together with the nitrogen atom to which they are attached form a 5 or 6 membered nitrogen containing heterocyclic ring containing up to 5 carbon ring atoms.

50. The salt according to claim 49 wherein $R_3$ is

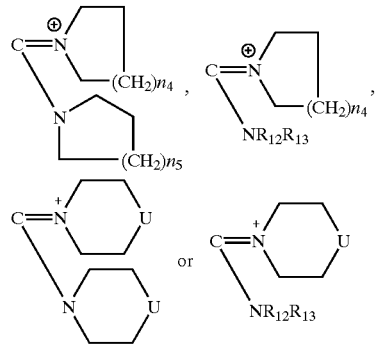

wherein

U is N-ALK, $CH_2$ or O;

ALK is lower alkyl or hydrogen;

$n_4$ and $n_5$ are independently 1 or 2; and $R_{12}$ and $R_{13}$ are independently hydrogen or lower alkyl.

51. The salt according to claim 50 wherein $R_3$ is

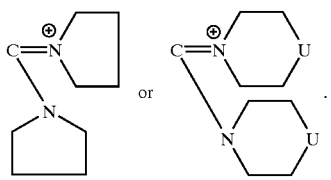 or 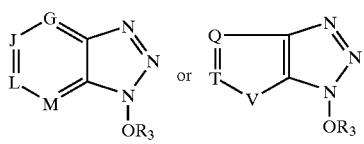

52. The salt according to claim 41 wherein A is unsubstituted.

53. The salt according to claim 1 wherein the cation is

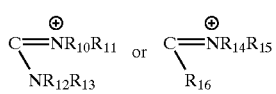

wherein

G is N or $CR_1$;

J is N or $CR_2$;

L is N or $CR_8$;

M is N or $CR_5$;

V is O, S or NH;

Q is N or $CR_6$;

T is N or $CR_7$;

$R_2$, $R_8$ and $R_5$, $R_6$ and $R_7$ are independently hydrogen or lower alkyl which may be unsubstituted or substituted with an electron donating group or electron withdrawing group;

$R_1$ is hydrogen;

E is N or CR;

R is hydrogen or lower alkyl;

$R_3$ is a positively charged electron withdrawing group having the formula:

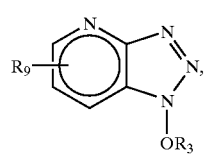

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing heterocyclic ring containing up to a total of 5 carbon ring atoms.

54. The salt according to claim 53 wherein the cation has the formula:

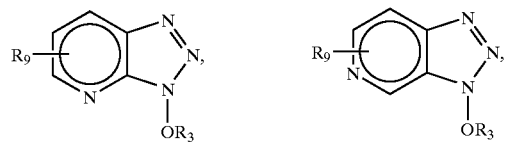

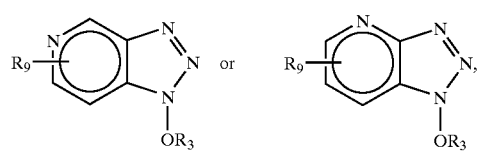

wherein $R_9$ is hydrogen, lower alkyl or electron donating or electron withdrawing group.

55. The salt according to claim 53 wherein the cation has the formula:

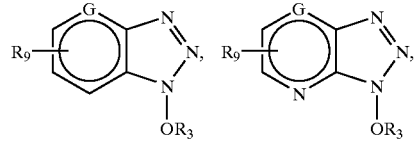

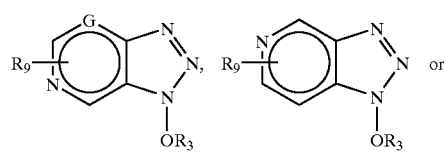

wherein $R_9$ is hydrogen, lower alkyl, or electron withdrawing group or electron donating group and G is N.

56. A salt formed from the reaction of $R_3Y$ and the salt of

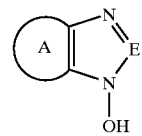

under substitution reaction conditions wherein

Y is a leaving group;

A is an oxygen, sulfur or nitrogen heterocyclic group wherein said heterocyclic group contains from 3 up to a total of 14 ring atoms and from 3 up to a total of 13 ring carbon atoms, and up to a total of 20 carbon atoms, said ring containing at least 1 heteroatom ring atom, said heteroatom present on the ring being selected from the group consisting of N and S, a nitrogen, oxygen or sulfur heteroaryl group wherein said heteroaryl ring is an oxygen, sulfur, or nitrogen containing heteroaromatic ring containing 5 to 14 ring atoms and up to a total of 4 to 13 ring carbon atoms and 20 carbon atoms, said heteroatom being selected from the group consisting of N, O, and S, which heterocyclic, aryl and heteroaryl groups are unsubstituted or substituted by lower alkyl, an electron withdrawing group or an electron donating group.

E is CR or N;

$R_3$ is a positively charged electron withdrawing group having the formula:

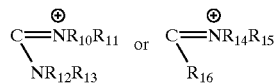

wherein $R_{10}$, $R_{11}$, $R_{12}$, $R_{13}$, $R_{14}$, $R_{15}$ and $R_{16}$ are independently hydrogen or lower alkyl which may be unsubstituted or substituted with an electron withdrawing or electron donating group or $R_{10}$ and $R_{12}$ taken together with the nitrogen atom to which they are attached and the carbon atom attached to both of said nitrogen atoms form a 5 or 6 membered nitrogen containing heterocyclic ring containing up to 4 carbon ring atoms; or $R_{10}$ and $R_{11}$ taken together with the nitrogen atom to which they are attached form a 5 or 6 membered nitrogen containing heterocyclic ring containing up to a total of 5 carbon ring atoms or $R_{12}$ and $R_{13}$ taken together with the nitrogen atom to which they are attached form a 5 or 6 membered nitrogen containing heterocyclic ring containing up to a total of 5 carbon ring atoms.

57. The salt according to claim 1 which is

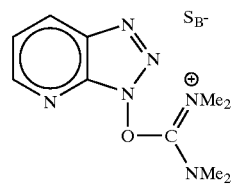

wherein $S_B$ is an anion.

58. The salt according to claim 1 which is

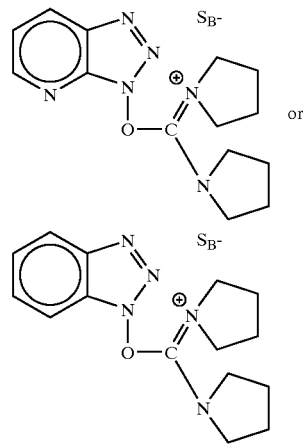

wherein $S_B$ is an anion.

59. A salt, wherein the cation is N-[dimethylamino](3H-1,2,3-triazolo-[4,5-c]isoquinolin-3-yl-oxy)-N-methyl methanaminium.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthesized
      Peptide

<400> SEQUENCE: 1

Val Gln Ala Ala Ile Asp Tyr Ile Asn Gly
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthesized
      Peptide
<220> FEATURE:
<221> NAME/KEY: UNSURE
<222> LOCATION: (2)
<223> OTHER INFORMATION: Xaa=Aib
<220> FEATURE:
<221> NAME/KEY: UNSURE
<222> LOCATION: (3)
<223> OTHER INFORMATION: Xaa=Aib

<400> SEQUENCE: 2

Tyr Xaa Xaa Phe Leu
1               5